(12) United States Patent
Lebhar et al.

(10) Patent No.: US 12,334,196 B1
(45) Date of Patent: Jun. 17, 2025

(54) MEDICAL DEVICE AND HEALTH INFORMATION TRACKING SYSTEMS AND METHODS

(71) Applicants: Michael Scott Lebhar, Jackson, MS (US); Marc Edward Walker, Jackson, MS (US)

(72) Inventors: Michael Scott Lebhar, Jackson, MS (US); Marc Edward Walker, Jackson, MS (US)

( * ) Notice: Subject to any disclaimer, the term of this patent is extended or adjusted under 35 U.S.C. 154(b) by 0 days.

(21) Appl. No.: 19/042,955

(22) Filed: Jan. 31, 2025

Related U.S. Application Data

(63) Continuation of application No. 18/760,245, filed on Jul. 1, 2024.

(51) Int. Cl.
| | |
|---|---|
| *G16H 10/20* | (2018.01) |
| *G16H 10/60* | (2018.01) |
| *G16H 40/40* | (2018.01) |
| *G16H 80/00* | (2018.01) |

(52) U.S. Cl.
CPC ............. *G16H 10/20* (2018.01); *G16H 10/60* (2018.01); *G16H 40/40* (2018.01); *G16H 80/00* (2018.01)

(58) Field of Classification Search
CPC ........ G16H 10/20; G16H 10/60; G16H 40/40; G16H 80/00
See application file for complete search history.

(56) References Cited

U.S. PATENT DOCUMENTS

| | | | |
|---|---|---|---|
| 2023/0268040 A1* | 8/2023 | Cordonnier | G16H 10/60 705/3 |
| 2024/0061951 A1* | 2/2024 | Innanje | G16H 50/20 |
| 2024/0420812 A1* | 12/2024 | Ramde | G16H 10/60 |

* cited by examiner

*Primary Examiner* — Khoi V Le
(74) *Attorney, Agent, or Firm* — Brian T. Sattizahn; Maynard Nexsen PC

(57) ABSTRACT

The medical device and health tracking system can generate non-fungible tokens (NFTs) associated with a user. NFTs can include information related to medical devices implanted within a user. In some embodiments, the NFT can include other health related information of the user. The NFTs can also be associated with items used within the medical supply chain that are used in medical interventions or procedures associated with the user. The medical device and health tracking system can track the manufacture, distribution, and use or implantation of a respective medical device by generating an NFT, transferring the NFT between different systems along the supply chain, and ultimately transferring the NFT to the end-user. The NFT may be updated as the associated medical device travels through the supply chain to include data regarding its manufacture, distribution, and use within the end user. Health conditions may also be tracked by the system.

16 Claims, 13 Drawing Sheets ically store information related to a physical object as a digital token which is recorded onto a blockchain system operated by a number of distributed nodes over a network. As long as at least one node remains operable, the information stored on the blockchain network is immutably stored. Examples of the present disclosure utilizes NFTs stored on a blockchain system to track medical device and medical health information associated with patients, which gives patients unprecedented access to, and control over their own medical information.

MEDICAL DEVICE AND HEALTH INFORMATION TRACKING SYSTEMS AND METHODS

CROSS-REFERENCE TO RELATED APPLICATION

This application is a continuation and claims priority to U.S. Nonprovisional application Ser. No. 18/760,245, entitled "MEDICAL DEVICE AND HEALTH INFORMATION TRACKING SYSTEMS AND METHODS" and filed on Jul. 1, 2024, which is incorporated herein by reference in its entirety.

FIELD

The disclosed technology relates to medical device tracking systems and methods. Specifically, this disclosed technology relates to medical device tracking systems and methods that track information related to the entire life cycle of a medical device and allow a patient to selectively share information related to a medical device with various third party entities.

BACKGROUND

Patients within the modern healthcare industry face a lack of information regarding treatments, implants, operations, and diagnoses. Healthcare providers record medical information related to treatment and diagnosis of patients within electronic health record (EMR) systems that are operated by healthcare provider systems (e.g., hospitals, doctor offices, etc.) but patients do not have direct access or control over their own health-related information. These problems are additionally compounded as it relates to medical devices that are implanted within patients. Patients receiving implantable devices such as knee replacements, hip replacements, breast implants, pacemakers, etc. face a lack of knowledge regarding the specifics of their own implants, such as manufacturer, model number, recall information, warranty information, etc. Often, the healthcare providers responsible for implanting the devices into patients do not keep accurate records of the specific implant information that was installed within a patient and patients are left without access to important medical information related to their implanted devices.

Accordingly, there is a need for improved systems and methods for medical device and medical health information tracking systems and methods.

BRIEF DESCRIPTION OF THE DRAWINGS

Reference will now be made to the accompanying drawings, which are not necessarily drawn to scale, and which illustrate various implementations, aspects, and principles of the disclosed technology. In the drawings.

DETAILED DESCRIPTION

Figure 1:
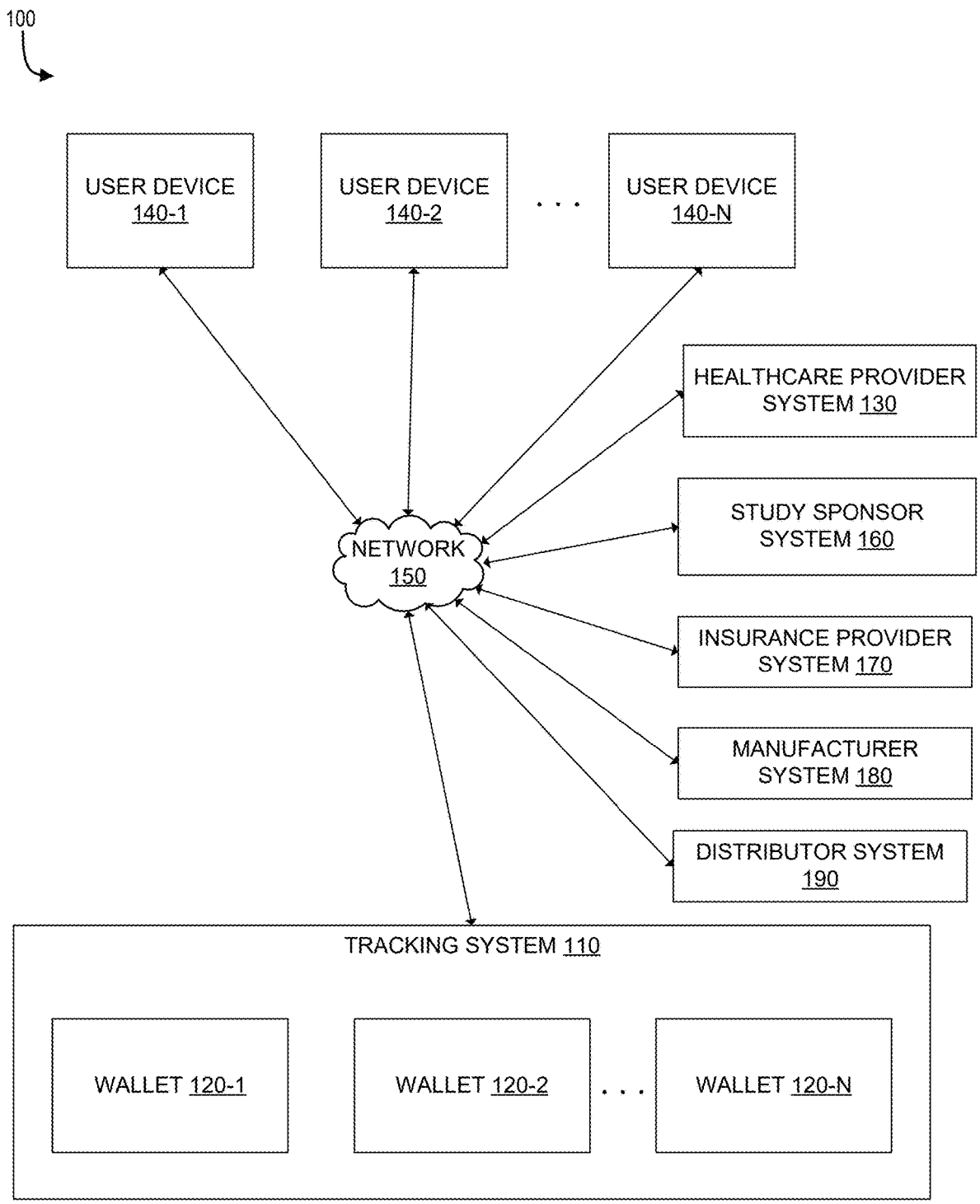
FIG. 1 is a block diagram of an example system that may be used to provide a medical device and health tracking system, according to an example implementation of the disclosed technology.

With the advent of blockchain technology non-fungible tokens (NFTs) it is now possible to immutably store information related to a physical object as a digital token which is recorded onto a blockchain system operated by a number of distributed nodes over a network. As long as at least one node remains operable, the information stored on the blockchain network is immutably stored. Examples of the present disclosure utilizes NFTs stored on a blockchain system to track medical device and medical health information associated with patients, which gives patients unprecedented access to, and control over their own medical information.

At a high level, some embodiments consistent with the disclosed systems and methods provide for a blockchain-enabled system that is capable of storing medical device and health related information of a patient on the blockchain in patient-specific wallet. Information associated with the entire lifecycle of a medical device can be recorded onto a wallet. For example, upon the creation of a medical device, the manufacturer can use a computing device (e.g., mobile phone, tablet, PC, etc.) to scan an identifier (e.g., QR code) associated with the medical device which includes information related to the medical device. The identifier can be used to create an NFT that is stored on a wallet (e.g., wallet 120, as described below) that can store all the medical device information provided by the manufacturer. As a non-limiting list, the manufacturer can include a medical device identifier (e.g., a serial number), a date of creation, a date of expiry, dimensional characteristics, company name, internal material, external material, digital warranty information, etc. Once the medical device moves to distribution, ownership of the NFT can be transferred from the manufacturer system to a distribution system, for example, by transferring to the NFT from a blockchain address associated with a wallet of the manufacturer system to a blockchain address associated with a wallet of the distributor. As the medical devices moves through the distribution process, the device is scanned by distribution centers and the NFT is updated with tracking information that identifies information related to the handling of the product at each stop along the distribution route. For example, the date and time, location, handing employee, etc. is recorded to the NFT at each stop along the distribution route. The medical device may be shipped to a healthcare provider center (e.g., a hospital) at which the device is scanned by an associate of the healthcare provider system. Upon arrival at the healthcare provider center, ownership of the NFT can be transferred from the distribution system to the healthcare provider system, for example, by transferring to the NFT from a blockchain address associated with a wallet of the distribution system to a blockchain address associated with a wallet of the healthcare provider system. The NFT may be updated with information related to the endpoint hospital, such as the hospital name, the requesting physician, the time and date the medical device is received, etc. Finally, when the medical device is ultimately implanted into a patient, the NFT can be again updated with additional information. Prior to the operation, for example, the surgeon may remove the medical device from the packaging, scan an identifier associated with the medical device, and update the NFT with additional information related to the type of operation, the time and date of the operation, etc. Upon implantation, ownership of the NFT can be transferred from the healthcare provider system to the patient, for example, by transferring to the NFT from a blockchain address associated with a wallet of the healthcare provider system to a blockchain address associated with a wallet of the patient.

In some embodiments, if the medical device is found to be defective by one or more associates of the hospital system, the NFT representing the medical device may be transferred to a "trash" inventory wallet that can be used to track defective medical device inventory.

In some embodiments, in order to authenticate or otherwise verify the chain of custody of a medical implant before a transfer of physical custody (e.g., transfer between a distributor, a shipping entity, a hospital system, and/or a patient), the medical device may be scanned by a plurality of users associated with the receiving entity. For example, prior to implantation, a medical device may be scanned by more than one user associated with a hospital system, such as one or more nurses, one or more doctors, and one or more hospital administrators. According to some embodiments, a threshold number of user devices may interact with (e.g., scan a QR code) a medical device to verify that the medical device is prepared for a physical custody transfer.

In some embodiments, if an associate of a respective entity (e.g., hospital system, distributor system, manufacturer system, etc.) becomes no longer associated with the entity, an administrator of the entity may transmit instructions to the medical device and health tracking system to de-register or otherwise de-associate the associate's devices from the entity.

In some embodiments, ownership of the NFT can be used to authenticate a patient, thereby allowing the patient to have access and ownership over additional medical information, such as data stored on a healthcare provider electronic medical record (EMR) system. EMR data can include patient-centric information, such as height, weight, blood type, blood pressure, existing diagnoses, allergies, etc. In some examples, the system may receive EMR data related to the patient following authentication, and may generate a second NFT that is stored in the wallet associated with the patient comprising the EMR data.

In some embodiments, the medical device and health tracking system allows patients greater control over their health information. For example, patient health information can be used to generate an NFT based on and including the patient health information. The patient can modify the health information, for example by provisionally including a diagnosis or health condition within their health information. In some embodiments, the system may transmit a request to a healthcare provider of the patient to validate the provisional diagnosis or health condition. In a similar manner, a healthcare provider can provisionally add a health related condition or diagnosis related to a patient which can be incorporated into the NFT associated with patient health related information stored on the patient wallet. The patient can review the data incorporated into the NFT, and can confirm the data or contest the data if the patient does not believe that the health related condition or diagnosis is accurate.

In some embodiments, manufacturers of medical devices can utilize the medical device and health tracking system to initiate recalls for medical devices tracked by the system. For example, a manufacturer can transmit a recall request to the system that can include information identifying a specific set of medical devices that are covered by the recall. The medical device and health tracking system can then compare the information identifying the specific set of medical devices within the recall request with the information stored within the NFTs associated with medical devices tracked by the system to identify medical devices that are covered under the recall. In response, patients can be notified regarding the recall request so that the patients can take appropriate action to replace or repair their medical devices.

In some embodiments, research institutions can utilize the medical device and health tracking system to initiate studies related to medical devices tracked by the system. For example, a research institution can transmit a study request to the system that can include information identifying a specific set of medical devices that are relevant to the study. The medical device and health tracking system can then compare the information identifying the specific set of medical devices within the study request with the information stored within the NFTs associated with medical devices tracked by the system to identify medical devices that are eligible for the study. In response, patients can be notified regarding compatibility with the study request. Patients can then choose to become involved in the study by sharing information related to their medical device and/or other health related data with the research institution. In some embodiments, in response to sharing their data with the research institution, the medical device and health tracking system can transmit, and patients can receive cryptocurrency tokens to their wallet.

In some embodiments, patients having medical devices can utilize the medical device and health tracking system to initiate warranty requests for their medical devices. For example, a patient can transmit a warranty request to the system including warranty information stored on the NFT associated with the medical device of the patient. The medical device and health tracking system can validate the warranty request based on warranty information stored within the NFT. After validation, the medical device and health tracking system can transmit the warranty request to a device associated with the manufacturer of the medical device to initiate the warranty of the medical device.

In some embodiments, the systems and methods described herein allow a user of the medical device and health tracking system to transfer an NFT associated with a medical device to another user, allowing another user to own the NFT while the medical implant remains implanted within the user. In some embodiments, the transferor may receive one or more cryptocurrency tokens in response to transferring the NFT to the transferee.

In some embodiments, the information stored within NFTs associated with a respective patient can be used to verify an identity of the patient. In other words, the patient can cause the medical device and health tracking system to selectively share certain NFT data entries within a patient's digital wallet with a third party, thereby allowing the third party to verify the identity of the patient.

Although the preceding embodiments discuss the use of an NFT to contain the information pertaining to a patient's heath conditions and/or implants, in other embodiments, the information may be encoded directly into blocks of the blockchain implemented by the medical device and health tracking system.

In another aspect of the invention, some embodiments consistent with the disclosed systems and methods provide for a system that is capable of storing medical device and health related information of a patient on a patient-specific wallet. Information associated with the entire lifecycle of a medical device can be recorded onto the wallet. For example, upon the creation of a medical device, the manufacturer can use a computing device (e.g., mobile phone, tablet, PC, etc.) to scan an identifier (e.g., QR code) associated with the medical device which includes information related to the medical device. The identifier can be used to generate and store one or more data entries on a wallet (e.g., wallet 720, as described below) that can store all the medical device information provided by the manufacturer. As a non-limiting list, the manufacturer can include a medical device identifier (e.g., a serial number), a date of creation, a date of expiry, dimensional characteristics, company name, internal material, external material, digital warranty information, etc. Once the medical device moves to distribution, ownership of the wallet can be transferred from the manufacturer system to a distribution system, for example, by transferring ownership of the wallet from the manufacturer system to the distributor system. As the medical devices moves through the distribution process, the device is scanned by distribution centers and the one or more data entries of the wallet are updated with tracking information that identifies information related to the handling of the product at each stop along the distribution route. For example, the date and time, location, handing employee, etc. is recorded to the wallet at each stop along the distribution route. The medical device may be shipped to a healthcare provider center (e.g., a hospital) at which the device is scanned by an associate of the healthcare provider system. Upon arrival at the healthcare provider center, ownership of the wallet can be transferred from the distribution system to the healthcare provider system. The one or more data entries within the wallet may be updated with information related to the endpoint hospital, such as the hospital name, the requesting physician, the time and date the medical device is received, etc. Finally, when the medical device is ultimately implanted into a patient, the one or more data entries of the wallet can be again updated with additional information. Prior to the operation, for example, the surgeon may remove the medical device from the packaging, scan an identifier associated with the medical device, and update the data entries within the wallet with additional information related to the type of operation, the time and date of the operation, etc. Upon implantation, ownership of the wallet can be transferred from the healthcare provider system to the patient.

In some embodiments, if the medical device is found to be defective by one or more associates of the hospital system, the one or more data entries within the wallet representing the medical device may be transferred to a "trash" inventory wallet that can be used to track defective medical device inventory.

In some embodiments, in order to authenticate or otherwise verify the chain of custody of a medical implant before a transfer of physical custody (e.g., transfer between a distributor, a shipping entity, a hospital system, and/or a patient), the medical device may be scanned by a plurality of users associated with the receiving entity. For example, prior to implantation, a medical device may be scanned by more than one user associated with a hospital system, such as one or more nurses, one or more doctors, and one or more hospital administrators. According to some embodiments, a threshold number of user devices may interact with (e.g., scan a QR code) a medical device to verify that the medical device is prepared for a physical custody transfer.

In some embodiments, if an associate of a respective entity (e.g., hospital system, distributor system, manufacturer system, etc.) becomes no longer associated with the entity, an administrator of the entity may transmit instructions to the medical device and health tracking system to de-register or otherwise de-associate the associate's devices from the entity.

In some embodiments, ownership of the wallet can be used to authenticate a patient, thereby allowing the patient to have access and ownership over additional medical information, such as data stored on a healthcare provider electronic medical record (EMR) system. EMR data can include patient-centric information, such as height, weight, blood type, blood pressure, existing diagnoses, allergies, etc. In some examples, the system may receive EMR data related to the patient following authentication, and may generate a second set of one or more data entries that are stored in the wallet associated with the patient, wherein the one or more data entries include the EMR data.

In some embodiments, the medical device and health tracking system allows patients greater control over their health information. For example, patient health information can be used to generate one or more data entries based on and including the patient health information, which is stored on a patient wallet. The patient can modify the health information, for example by provisionally including a diagnosis or health condition within their health information. In some embodiments, the system may transmit a request to a healthcare provider of the patient to validate the provisional diagnosis or health condition. In a similar manner, a healthcare provider can provisionally add a health related condition or diagnosis related to a patient which can be incorporated into the data entries within the wallet. The patient can review the data incorporated into the wallet, and can confirm the data or contest the data if the patient does not believe that the health related condition or diagnosis is accurate.

In some embodiments, manufacturers of medical devices can utilize the medical device and health tracking system to initiate recalls for medical devices tracked by the system. For example, a manufacturer can transmit a recall request to the system that can include information identifying a specific set of medical devices that are covered by the recall. The medical device and health tracking system can then compare the information identifying the specific set of medical devices within the recall request with the information stored within the data entries associated with medical devices tracked by the system to identify medical devices that are covered under the recall. In response, patients can be notified regarding the recall request so that the patients can take appropriate action to replace or repair their medical devices.

In some embodiments, research institutions can utilize the medical device and health tracking system to initiate studies related to medical devices tracked by the system. For example, a research institution can transmit a study request to the system that can include information identifying a specific set of medical devices that are relevant to the study. The medical device and health tracking system can then compare the information identifying the specific set of medical devices within the study request with the information stored within the wallets associated with medical devices tracked by the system to identify medical devices that are eligible for the study. In response, patients can be notified regarding compatibility with the study request. Patients can then choose to become involved in the study by sharing information related to their medical device and/or other health related data with the research institution. In some embodiments, in response to sharing their data with the research institution, the medical device and health tracking system can transmit, and patients can receive compensation from the receiving party.

In some embodiments, patients having medical devices can utilize the medical device and health tracking system to initiate warranty requests for their medical devices. For example, a patient can transmit a warranty request to the system including warranty information stored as the data entries within the wallet associated with the medical device of the patient. The medical device and health tracking system can validate the warranty request based on warranty information stored as the data entries within the wallet. After validation, the medical device and health tracking system can transmit the warranty request to a device associated with the manufacturer of the medical device to initiate the warranty of the medical device.

In some embodiments, the systems and methods described herein allow a user of the medical device and health tracking system to transfer a wallet associated with a medical device to another user, allowing a different user to own the wallet while the medical implant remains implanted within the user. In some embodiments, the transferor may receive compensation from the receiving party.

In some embodiments, the information stored as the data entries within wallets associated with a respective patient can be used to verify an identity of the patient. In other words, the patient can cause the medical device and health tracking system to selectively share certain data entries within a patient's digital wallet with a third party, thereby allowing the third party to verify the identity of the patient.

Some implementations of the disclosed technology will be described more fully with reference to the accompanying drawings. This disclosed technology may, however, be embodied in many different forms and should not be construed as limited to the implementations set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods.

Reference will now be made in detail to example embodiments of the disclosed technology that are illustrated in the accompanying drawings and disclosed herein. Wherever convenient, the same reference numbers will be used throughout the drawings to refer to the same or like parts.

FIG. 1 is a block diagram of an example medical device and health tracking system 100, according to an example implementation of the disclosed technology. The components and arrangements shown in FIG. 1 are not intended to limit the disclosed embodiments as the components used to implement the disclosed processes and features may vary. As shown, medical device and health tracking system 100 may include a tracking system 110 that operates on a number of nodes 210-1, 210-2, . . . , 210-N (discussed in more detail with respect to FIG. 2), one or more wallets 120-1, 120-2, . . . , 120-N stored on the tracking system 110, one or more user devices 140-1, 140-2, . . . , 140-N, a healthcare provider system 130, a study sponsor system 160, an insurance provider system 170, a manufacturer system 180, and a distributor system 190, all connected by network 150.

In some embodiments, a user may operate the user device 140. The user device 140 can include one or more of a mobile device, smart phone, general purpose computer, tablet computer, laptop computer, telephone, public switched telephone network (PSTN) landline, smart wearable device, voice command device, other mobile computing device, or any other device capable of communicating with the network 150 and ultimately communicating with one or more components of the medical device and health tracking system 100. In practice, user devices 140 can be configured to communicate with tracking system 110 in order to make cryptographic commitments to medical device and health tracking system 100. Cryptographic commitments, in its most general sense, are instructions recorded on the tracking system 110 that can include the generation, transfer, and/or modification of non-fungible tokens (NFTs) that are stored in cryptographic addresses of the tracking system 110. In certain example embodiments, the cryptographic commitments made by users can be used to generate NFTs that comprise data related to a medical device that may be implanted within a user of a respective user device 140. In some embodiments, the cryptographic commitments made by users can be used to generate NFTs that comprise data related to a user's health information, such as diagnoses, or health related conditions. Tracking system 110 can be of any type, for example a public blockchain, a private blockchain, a semiprivate blockchain etc. In certain embodiments, blockchain 110 includes smart contract functionality that enables the operation of medical device and health tracking system 100. In certain non-limiting embodiments, the blockchain 110 may comprise the Ethereum blockchain.

Users may include individuals such as, for example, subscribers, clients, prospective clients, or customers of medical device and health tracking system 100. According to some embodiments, the user device 140 may include an environmental sensor for obtaining audio or visual data, such as a microphone and/or digital camera, a geographic location sensor for determining the location of the device, an input/output device such as a transceiver for sending and receiving data, a display for displaying digital images, one or more processors, and a memory in communication with the one or more processors.

The network 150 may be of any suitable type, including individual connections via the internet such as cellular or WiFi networks. In some embodiments, the network 150 may connect terminals, services, and mobile devices using direct connections such as radio-frequency identification (RFID), near-field communication (NFC), Bluetooth™, low-energy Bluetooth™ (BLE), WiFi™, ZigBee™, ambient backscatter communications (ABC) protocols, USB, WAN, or LAN. Because the information transmitted may be personal or confidential, security concerns may dictate one or more of these types of connections be encrypted or otherwise secured. In some embodiments, however, the information being transmitted may be less personal, and therefore the network connections may be selected for convenience over security.

The network 150 may include any type of computer networking arrangement used to exchange data. For example, the network 150 may be the Internet, a private data network, virtual private network (VPN) using a public network, and/or other suitable connection(s) that enable(s) components in the medical device and health tracking system 100 to send and receive information. The network 150 may also include a PSTN and/or a wireless network.

Wallets 120 can be configured to store NFTs of respective users on the tracking system 110. Each wallet 120 can be associated with a respective user of tracking system 110, although in some embodiments, a single user may be associated with more than one wallet 120. Each wallet 120 can be configured to generate blockchain addresses which can receive cryptographic tokens, including NFTs. The user associated with a respective wallet 120 can view, transfer, and/or modify tokens associated with blockchain addresses of the respective wallet 120, while other users of tracking system 110 may only be able to view the contents of the blockchain addresses of respective wallet 120 without the ability to transfer or modify the tokens.

Healthcare provider system 130 can be associated with a hospital, clinic, urgent care center, etc. Healthcare provider system 130 can be used by a representative of a hospital, clinic, etc., such as a doctor, nurse, or other healthcare administrator. The healthcare provider system can be used to transfer health related information to tracking system 110 to allow medical device and health tracking system 100 to generate a NFT that can be stored in a blockchain address of a wallet 120 of a respective user of medical device and health tracking system 100. In certain embodiments, the healthcare provider system 130 can store patient data related to diagnoses and/or health conditions in an EMR database. Upon authentication of a user, the healthcare provider system 130 can transmit such patient data to the tracking system 110 to allow medical device and health tracking system 100 to generate an NFT containing the patient data. The patient data can be stored on a blockchain address associated with a wallet 120 of the patient, thereby giving the patient direct access to their own patient information.

Study sponsor system 160 can be associated with a research institution, a university, a non-profit, etc. that is seeking to conduct studies related to medical devices. In certain example embodiments, study sponsor system 160 can transmit study requests to tracking system 110 to allow medical device and health tracking system 100 to record the study request to the blockchain. The medical device and health tracking system 100 can then determine, based on the study request, whether a medical device NFT associated with a respective wallet 120 matches the study request parameters. For example, the study request can be associated with a specific brand, serial number, or type of medical device. The medical device and health tracking system 100 can determine whether any wallet 120 includes a medical device matching the parameters of the study request, and transmit a notification to a user device associated with the respective wallet 120. In this regard, the medical device and health tracking system 100 enables a user to be notified when a study exists associated with a medical device that is associated with the user.

Insurance provider system 170 can be associated with a health insurance provider. In certain example embodiments, the medical device and health tracking system 100 can grant access to the insurance provider system 170 to NFT data stored on tracking system 110, thereby allowing insurance provider system 170 to determine the statistics surrounding what medical devices are being implanted into users. In some embodiments, the medical device and health tracking system 100 can determine statistical data associated with geographic distribution, demographic distribution, associated comorbidities, etc. associated with each type of medical device being represented by the NFTs stored on tracking system 110. In some embodiments, the medical device and health tracking system 100 can transmit the determined statistical data to the insurance provider system 170.

Manufacturer system 180 can be associated with the manufacturer of a respective medical device, and in some embodiments, can provide warranty coverage for a respective medical device. Upon creation of a medical device, the manufacturer (via manufacturer system 180) can interact with medical device and health tracking system 100 to create an NFT that contains digital data describing the medical device. In certain embodiments, the manufacturer system 180 can also be used to initiate warranties and recalls of the medical device via medical device and health tracking system 100.

Distributor system 190 can be associated with a distributor of a respective medical device. Although shown in FIG. 1 as one distributor system, it should be understood that in some embodiments, multiple distributors independently operating distributor systems 190-1, 190-2, . . . , 190-N can be included within medical device and health tracking system 100. Distributor system 190 can be utilized by distributors to update the NFT associated with a medical device to include tracking information, for example, the date and time a certain medical device arrives at a distribution center, the location of the distribution center, etc., as the medical device proceeds through distribution towards the hospital, surgeon center, and/or clinic where it may be implanted into a user.

Figure 7:
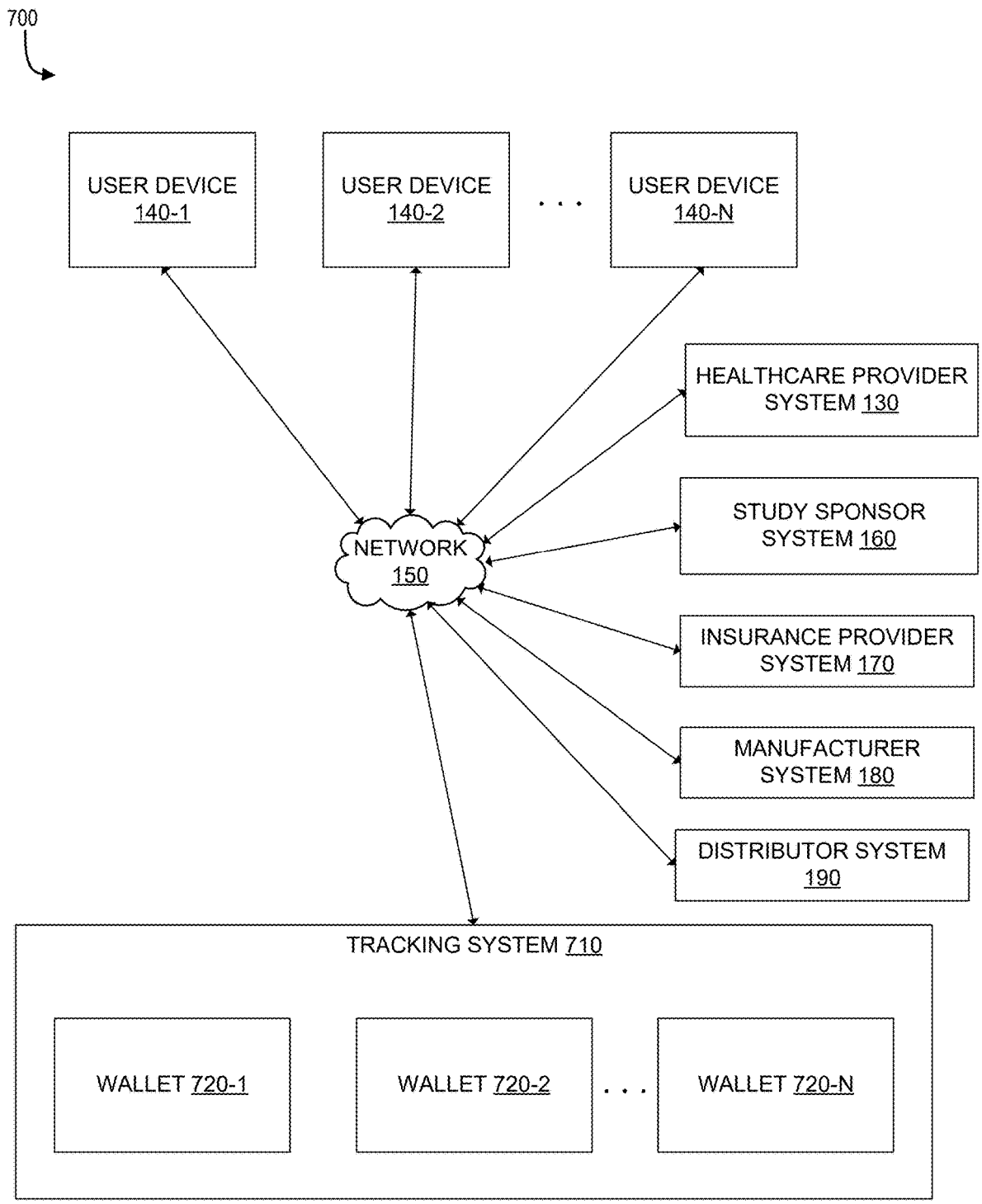
FIG. 7 is a block diagram of an example system that may be used to provide a medical device and health tracking system, according to an example implementation of the disclosed technology, in accordance with certain embodiments of the disclosed technology.

In contrast to the example block diagram of medical device and health tracking system 100, FIG. 7 discloses an alternative embodiment showing medical device and health tracking system 700. Medical device and health tracking system 700 is similar to medical device and health tracking system 100, except that tracking system 110 is replaced with tracking system 710, which is discussed in more detail with respect to FIG. 8.

Embodiments consistent with the present disclosure may include datasets. Datasets may comprise actual data reflecting real-world conditions, events, and/or measurements. However, in some embodiments, disclosed systems and methods may fully or partially involve synthetic data (e.g., anonymized actual data or fake data). Datasets may involve numeric data, text data, and/or image data. For example, datasets may include transaction data, financial data, demographic data, public data, government data, environmental data, traffic data, network data, transcripts of video data, genomic data, proteomic data, and/or other data associated with cryptographic commitments made by user devices 140 to the tracking system 110. Datasets of the embodiments may be in a variety of data formats including, but not limited to, PARQUET, AVRO, SQLITE, POSTGRESQL, MYSQL, ORACLE, HADOOP, CSV, JSON, PDF, JPG, BMP, and/or other data formats.

Although the preceding description describes various functions of user device 140, tracking system 110, wallet 120, healthcare provider system 130, study sponsor system 160, insurance provider system 170, manufacturer system 180, and distributor system 190 in some embodiments, some or all of these functions may be carried out by a single computing device.

Figure 2:
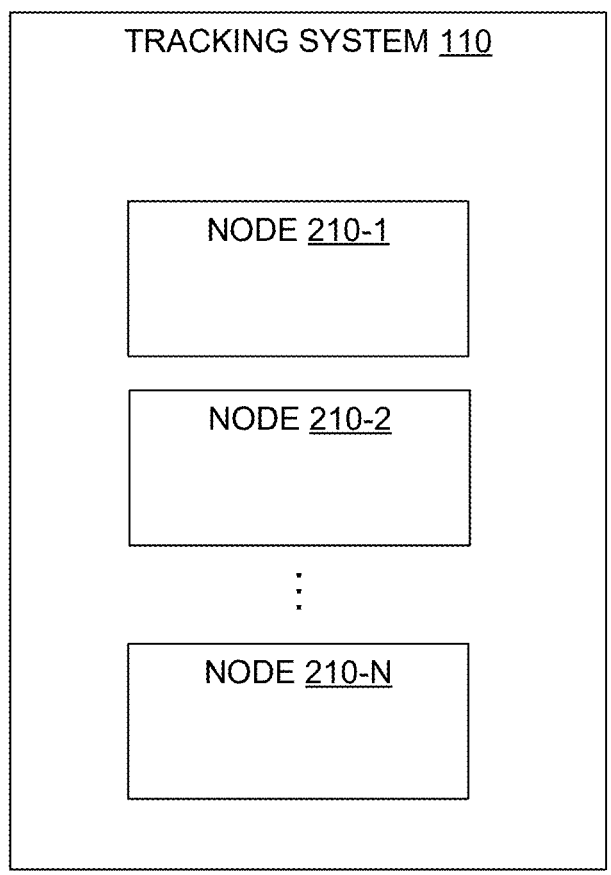
FIG. 2 is a block diagram of an example blockchain system used to provide medical device and health tracking system, according to an example implementation of the disclosed technology.

FIG. 2 is a block diagram of an example tracking system 110 used to provide a decentralized processing network, according to an example implementation of the disclosed technology. As described above with respect to FIG. 1, aspects of the medical device and health tracking system 100 can be implemented across a distributed web of computers, operating as nodes. FIG. 2 shows that tracking system 110 is implemented across a plurality of nodes 210 (e.g., nodes 210-1, 210-2, . . . , 210-N). Nodes 210 each include memory containing program instructions necessary to implement the protocol used by the tracking system 110 and medical device and health tracking system 100. It should be understood that in some embodiments, each node 210 can be controlled by a single entity (e.g., tracking system 110). Stated another way, tracking system 110 can be implemented as a permissioned blockchain that can only be modified (e.g., by adding additional blocks) by permissioned users of tracking system 110.

Figure 3:
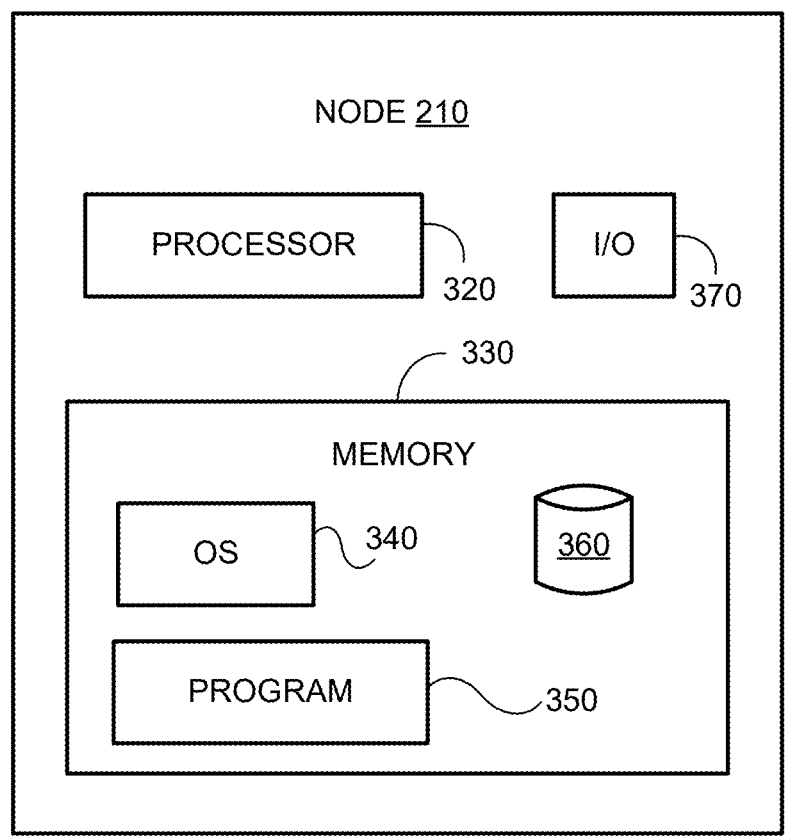
FIG. 3 is a block diagram of an example node used to enable the functionality of the blockchain system, according to an example implementation of the disclosed technology.
Figure 8:
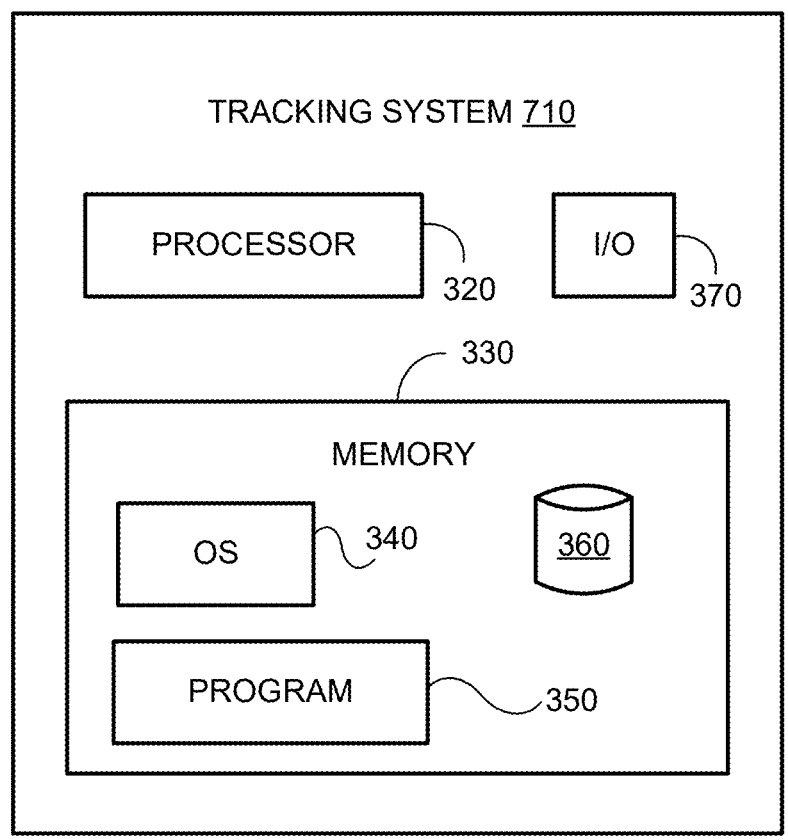
FIG. 8 is a block diagram of an example blockchain system used to provide medical device and health tracking system, according to an example implementation of the disclosed technology.

FIG. 3 is a block diagram of an example node 210 used to enable the functionality of the tracking system 110, according to an example implementation of the disclosed technology. According to some embodiments, healthcare provider system 130, study sponsor system 160, insurance provider system 170, manufacturer system 180, distributor system 190, and user devices 140, as depicted in FIGS. 1-2 and described above, may have a similar structure and components that are similar to those described with respect to node 210 shown in FIG. 3. As shown, the node 210 may include a processor 320, an input/output (I/O) device 370, a memory 330 containing an operating system (OS) 340 and a program 350. In certain example implementations, the node 210 may be a single server or may be configured as a distributed computer system including multiple servers or computers that interoperate to perform one or more of the processes and functionalities associated with the disclosed embodiments. In some embodiments node 210 may be one or more servers from a serverless or scaling server system. In some embodiments, the node 210 may further include a peripheral interface, a transceiver, a mobile network interface in communication with the processor 320, a bus configured to facilitate communication between the various components of the node 210, and a power source configured to power one or more components of node 210. Turning to FIG. 8, tracking system 710 has a similar structure and components as described above and below with respect to FIG. 3.

A peripheral interface, for example, may include the hardware, firmware and/or software that enable(s) communication with various peripheral devices, such as media drives (e.g., magnetic disk, solid state, or optical disk drives), other processing devices, or any other input source used in connection with the disclosed technology. In some embodiments, a peripheral interface may include a serial port, a parallel port, a general-purpose input and output (GPIO) port, a game port, a universal serial bus (USB), a micro-USB port, a high-definition multimedia interface (HDMI) port, a video port, an audio port, a Bluetooth™ port, a near-field communication (NFC) port, another like communication interface, or any combination thereof.

In some embodiments, a transceiver may be configured to communicate with compatible devices and ID tags when they are within a predetermined range. A transceiver may be compatible with one or more of: radio-frequency identification (RFID), near-field communication (NFC), Bluetooth™, low-energy Bluetooth™ (BLE), WiFi™, ZigBee™, ambient backscatter communications (ABC) protocols or similar technologies.

A mobile network interface may provide access to a cellular network, the Internet, or another wide-area or local area network. In some embodiments, a mobile network interface may include hardware, firmware, and/or software that allow(s) the processor(s) 320 to communicate with other devices via wired or wireless networks, whether local or wide area, private or public, as known in the art. A power source may be configured to provide an appropriate alternating current (AC) or direct current (DC) to power components.

The processor 320 may include one or more of a microprocessor, microcontroller, digital signal processor, co-processor or the like or combinations thereof capable of executing stored instructions and operating upon stored data. The memory 330 may include, in some implementations, one or more suitable types of memory (e.g. such as volatile or non-volatile memory, random access memory (RAM), read only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like), for storing files including an operating system, application programs (including, for example, a web browser application, a widget or gadget engine, and or other applications, as necessary), executable instructions and data. In one embodiment, the processing techniques described herein may be implemented as a combination of executable instructions and data stored within the memory 330.

The processor 320 may be one or more known processing devices, such as, but not limited to, a microprocessor from the Core™ family manufactured by Intel™, the Ryzen™ family manufactured by AMD™, or a system-on-chip processor using an ARM™ or other similar architecture. The processor 320 may constitute a single core or multiple core processor that executes parallel processes simultaneously, a central processing unit (CPU), an accelerated processing unit (APU), a graphics processing unit (GPU), a microcontroller, a digital signal processor (DSP), a field-programmable gate array (FPGA), an application-specific integrated circuit (ASIC) or another type of processing component. For example, the processor 320 may be a single core processor that is configured with virtual processing technologies. In certain embodiments, the processor 320 may use logical processors to simultaneously execute and control multiple processes. The processor 320 may implement virtual machine (VM) technologies, or other similar known technologies to provide the ability to execute, control, run, manipulate, store, etc. multiple software processes, applications, programs, etc. One of ordinary skill in the art would understand that other types of processor arrangements could be implemented that provide for the capabilities disclosed herein.

In accordance with certain example implementations of the disclosed technology, the node 210 may include one or more storage devices configured to store information used by the processor 320 (or other components) to perform certain functions related to the disclosed embodiments. In one example, the node 210 may include the memory 330 that includes instructions to enable the processor 320 to execute one or more applications, such as server applications, network communication processes, and any other type of application or software known to be available on computer systems. Alternatively, the instructions, application programs, etc. may be stored in an external storage or available from a memory over a network. The one or more storage devices may be a volatile or non-volatile, magnetic, semiconductor, tape, optical, removable, non-removable, or other type of storage device or tangible computer-readable medium.

The node 210 may include a memory 330 that includes instructions that, when executed by the processor 320, perform one or more processes consistent with the functionalities disclosed herein. Methods, systems, and articles of manufacture consistent with disclosed embodiments are not limited to separate programs or computers configured to perform dedicated tasks. For example, the node 210 may include the memory 330 that may include one or more programs 350 to perform one or more functions of the disclosed embodiments. For example, in some embodiments, the node 210 may additionally manage cryptographic commitments to generate, transfer, and/or modify tokens (including NFTs) received by tracking system 110 from user devices 140 via a program 350.

Similarly, as shown in FIG. 8, tracking system 710 may include a memory 330 that includes instructions that, when executed by the processor 320, perform one or more processes consistent with the functionalities disclosed herein. Methods, systems, and articles of manufacture consistent with disclosed embodiments are not limited to separate programs or computers configured to perform dedicated tasks. For example, the tracking system 710 may include the memory 330 that may include one or more programs 350 to perform one or more functions of the disclosed embodiments. For example, in some embodiments, the tracking system 710 may additionally manage storage of data entries within a user-specific wallet received by tracking system 710 from user devices 140 via a program 350.

The processor 320 may execute one or more programs 350 located remotely from the node 210. For example, the node 210 may access one or more remote programs that, when executed, perform functions related to disclosed embodiments.

The memory 330 may include one or more memory devices that store data and instructions used to perform one or more features of the disclosed embodiments. The memory 330 may also include any combination of one or more databases controlled by memory controller devices (e.g., server(s), etc.) or software, such as document management systems, Microsoft™ SQL databases, SharePoint™ databases, Oracle™ databases, Sybase™ databases, or other relational or non-relational databases. The memory 330 may include software components that, when executed by the processor 320, perform one or more processes consistent with the disclosed embodiments. In some embodiments, the memory 330 may include a database 360 for storing related data to enable the node 210 to perform one or more of the processes and functionalities associated with the disclosed embodiments.

The node 210 may also be communicatively connected to one or more memory devices (e.g., databases) locally or through a network. The remote memory devices may be configured to store information and may be accessed and/or managed by the node 210. By way of example, the remote memory devices may be document management systems, Microsoft™ SQL database, SharePoint™ databases, Oracle™ databases, Sybase™ databases, or other relational or non-relational databases. Systems and methods consistent with disclosed embodiments, however, are not limited to separate databases or even to the use of a database.

The node 210 may also include one or more I/O devices 370 that may comprise one or more interfaces for receiving signals or input from devices and providing signals or output to one or more devices that allow data to be received and/or transmitted by the node 210. For example, the node 210 may include interface components, which may provide interfaces to one or more input devices, such as one or more keyboards, mouse devices, touch screens, track pads, trackballs, scroll wheels, digital cameras, microphones, sensors, and the like, that enable the node 210 to receive data from a user (such as, for example, via the user device 140).

In examples of the disclosed technology, the node 210 may include any number of hardware and/or software applications that are executed to facilitate any of the operations. The one or more I/O interfaces may be utilized to receive or collect data and/or user instructions from a wide variety of input devices. Received data may be processed by one or more computer processors as desired in various implementations of the disclosed technology and/or stored in one or more memory devices.

While the node 210 has been described as one form for implementing the techniques described herein, other, functionally equivalent, techniques may be employed. For example, some or all of the functionality implemented via executable instructions may also be implemented using firmware and/or hardware devices such as application specific integrated circuits (ASICs), programmable logic arrays, state machines, etc. Furthermore, other implementations of the node 210 may include a greater or lesser number of components than those illustrated.

Figure 4:
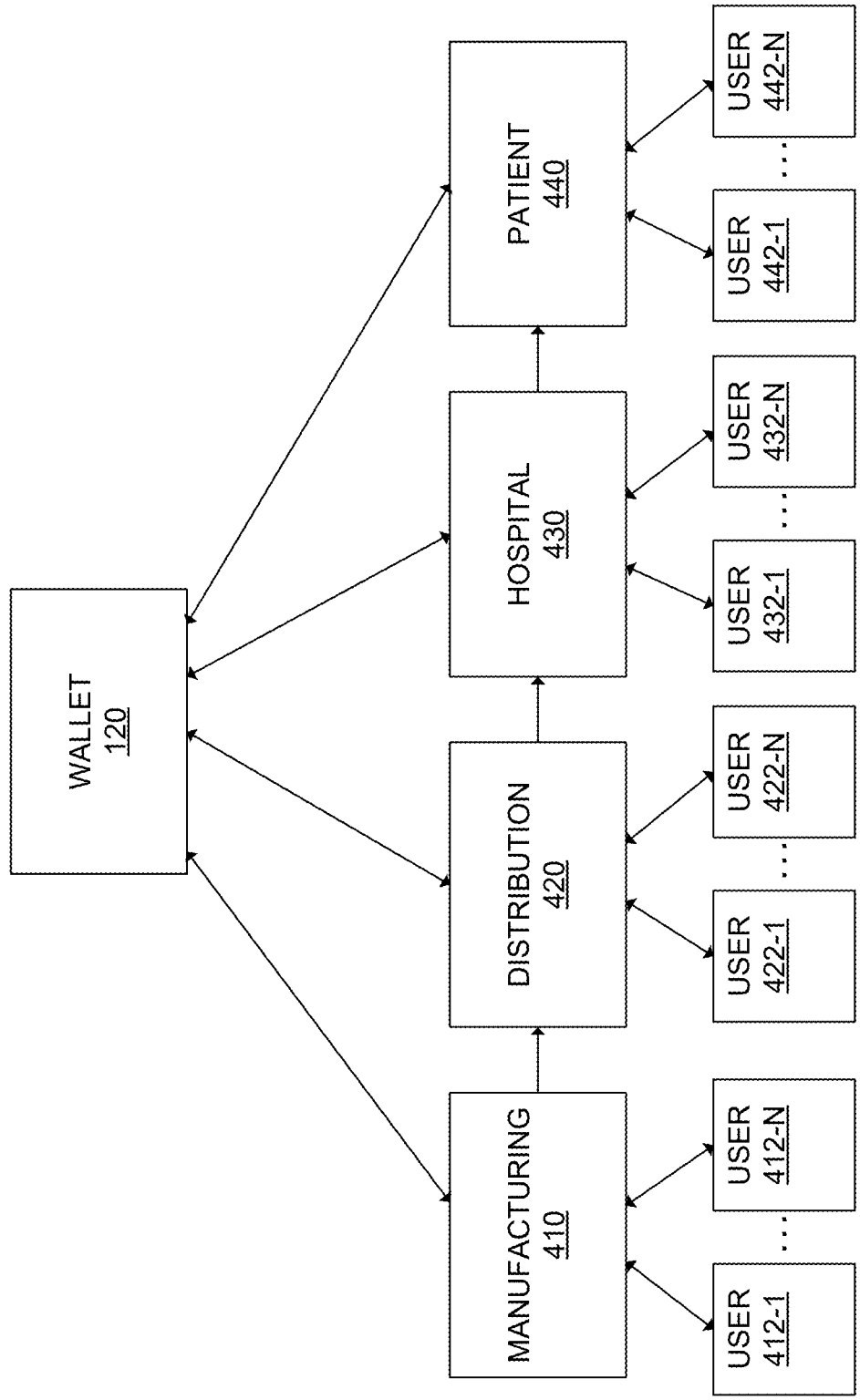
FIG. 4 is a block diagram illustrating how a medical device and health tracking system can track each event within a lifecycle of a medical device within a medical device wallet of the blockchain system, according to an example implementation of the disclosed technology.

FIG. 4 is a block diagram illustrating how a medical device and health tracking system can track each event within a lifecycle of a medical device within a medical device wallet of the blockchain system, according to an example implementation of the disclosed technology. FIG. 4 shows how an example medical device tracked by the medical device and health tracking system 100 can move between entities such as manufacturing 410, distribution 420, hospital 430, and patient 440. It should be noted that each entity includes one or more users that are able to interact with medical device and health tracking system 100 to provide verification and/or authentication of physical custody transfers of medical devices between the entities as well as other events requiring authentication, such as adding a health condition of a patient to a patient wallet. For example, the manufacturing entity 410 can be associated with one or more users 412, the distribution entity 420 can be associated with one or more users 422, the hospital entity can be associated with one or more users 432, and the patient can be associated with one or more users 442. Each user 412, 422, 432, and 442 can be associated with a respective user device 140, but in some embodiments, only users associated with a respective entity can provide verification and authentication of certain events. For example, one or more users 432 associated with hospital entity 430 may be require to interact with a medical device (e.g., via scanning a QR code) before being physical custody may be transferred from a distributor (e.g., distributor system 190) to a hospital (e.g., healthcare provider system 130). Users 412, 422, and 432 may be respective employees or contractors of manufacturer system 180, distributor system 190, and healthcare system 130, respectively. Users 442 may include the patient, as well as family members or other representatives granted the authority to have control and/or access to over patient data.

Figure 9:
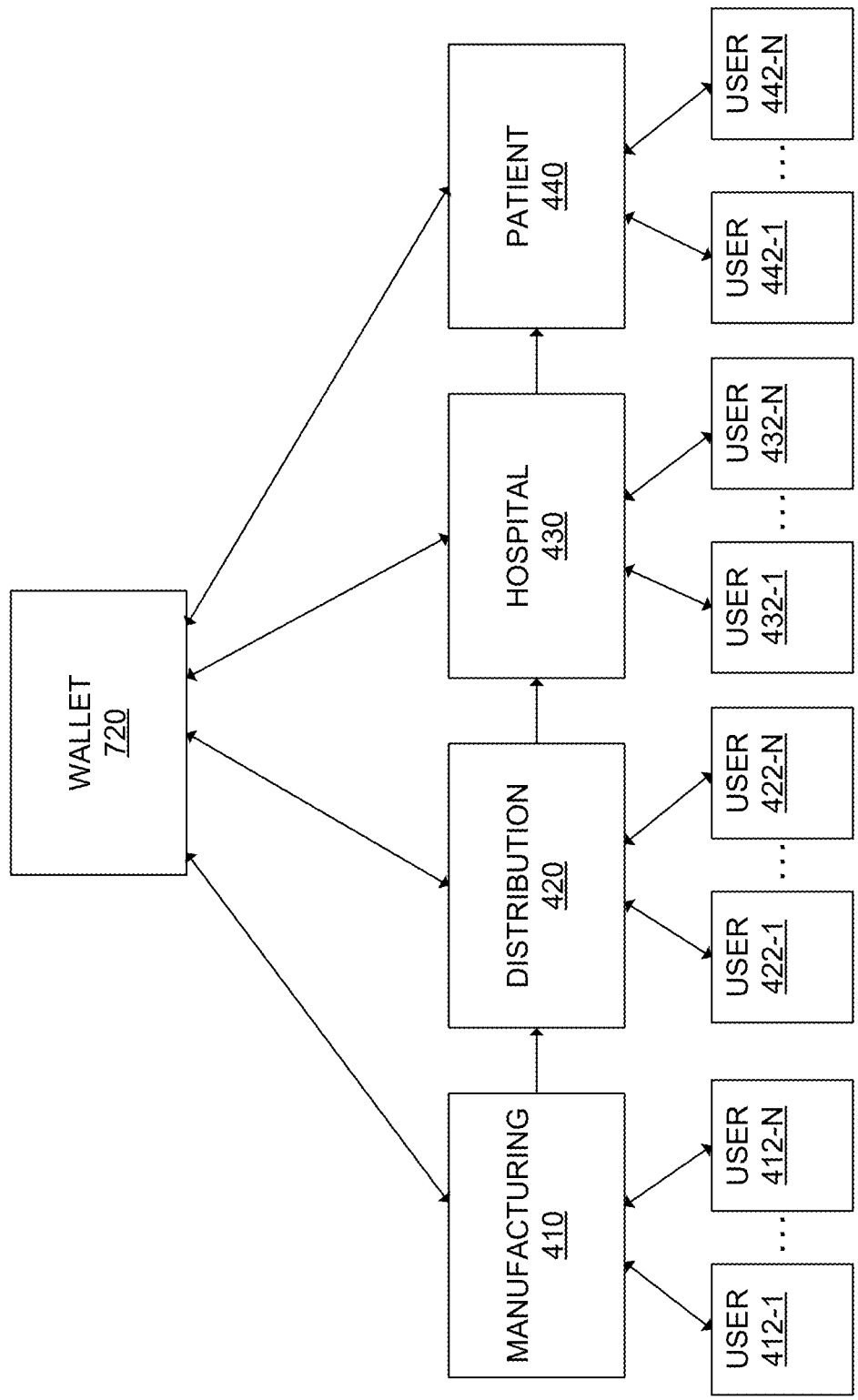
FIG. 9 is a block diagram illustrating how a medical device and health tracking system can track each event within a lifecycle of a medical device within a medical device wallet of the blockchain system, according to an example implementation of the disclosed technology.

In contrast to FIG. 4, FIG. 9 discloses an alternative embodiment showing the lifecycle of a medical device being tracked by medical device and health tracking system 700. The lifecycle shown in FIG. 9 is similar to what is described with respect to FIG. 4, except that data entries (in contrast to NFTs) associated with a patient and/or a medical device for implantation into a patient are stored within wallet 720. It should be understood that except for not implementing an NFT data structure, wallet 720 includes the same functionality as wallet 120 described herein.

As shown in the lifecycle of FIG. 4, a manufacturer (e.g., via manufacturer system 180) may manufacture a medical device which may be paired to the creation of an NFT within medical device and health tracking system 100. For example, upon the creation of a medical device, the manufacturer may transmit medical device data to the medical device and tracking system 100 which can be used to generate an NFT of the medical device within a wallet 120 (e.g., wallet 120-1) associated with the manufacture system 180. The medical device and tracking system 100 can generate the NFT and store the NFT at a first blockchain address that is associated with and generated by the respective wallet 120 (e.g., wallet 120-1). The NFT can include data associated with the respective medical device that is manufactured by the manufacture system 180. The NFT may include a serial code uniquely identifying the medical device, it may include a brand and model number, a date of creation, a date of expiry, dimensional values of the medical device, material types used, etc. In some examples, the medical device may be a breast implant device, and may include additional information such as the size, base width, projection, internal material type, external shell type, etc. It should be understood that the information stored within the NFT is not expressly limited to the above examples, and could include more information pertaining to the specific medical device being manufactured by manufacturer system 180. In some embodiments, the NFT can also include information related to a warranty provided by manufacturer system 180 for the medical device being produced. In this regard, the NFT stored on wallet 120-1 can contain warranty information, such as how long from the date of manufacture the medical device is warrantied for, which, along with data related to the date of manufacturer, can be used by medical device and health tracking system 100 to determine whether a respective medical device remains under warranty at any given point in time. In some embodiments, the NFT can contain additional warranty information, such as additional conditions that should be met to qualify the medical device for a warranty, for example, a verified physician's checkup every year, etc. The NFT can also include data necessary to initiate a warranty claim by an end user once the medical device is implanted into a patient and the NFT is transferred to the wallet 120 of a patient, as described in further detail below. In some embodiments, the medical device and health tracking system 100 may include smart contract functionality which can enable an end user (e.g., a patient) to initiate a warranty claim for a medical device with the manufacturer system 180.

The manufacturer of the medical device can provide appropriate packaging that includes an indicator on the package, such as a QR code, that uniquely links the medical device to the NFT contained within the wallet 120-1 associated with the manufacturer system 180. It should be understood that in some embodiments, the medical device itself can include a QR code also uniquely linking the medical device to the NFT stored within wallet 120-1. The manufacturer may release the medical device to a distributor for distribution to a healthcare provider such as a hospital or clinic for implantation into an end user (patient). In this regard, the manufacturer system 180 may send instructions to the medical device and health tracking system 100 to transfer the NFT to a wallet 120 (e.g., wallet 120-2) that is associated with distributor system 190. The distributor system 190 may scan the indicator (e.g., QR code) on the packaging of the medical device, and update the NFT with additional information associated with tracking the medical device as the medical device makes its way through distribution. The distribution system 190 may also track current inventory of medical devices being shipped via monitoring of the all the NFTs present within wallets1 120 (e.g., 120-2) associated with the distribution system 190. In some embodiments, distribution system 190 may undergo a regular (e.g., weekly, monthly, quarterly, etc.) updating of current inventory of medical devices within the distributor's control by scanning indicators (QR codes) that update the NFTs within wallet 120-2. Additionally, once the NFTs leave the custody of the distributor, NFTs are transferred out of wallet 120-2 associated with distributor system 190. In this regard, when the medical device arrives at the healthcare provider, the distributor may utilize the distributor system 190 to transfer the NFT from wallet 120-2 associated with the distributor system 190 to a wallet 120 (e.g., wallet 120-3) associated with the healthcare provider system 130.

Once the NFT is transferred to wallet 120-3 associated with healthcare provider system 130, the medical device may be assessed prior to implantation. In the event that the medical device is found to be defective, the healthcare provider system 130 can transmit instructions to transfer the NFT of the defective device into a new wallet 120 (e.g., wallet 120-4) associated with "defective" or "out of inventory" medical devices. In a similar manner, if a patient comes to the healthcare provider to have a medical device removed for any reason (e.g., a product recall, a defective implant, an implant failure, etc.), the patient may transfer the medical device NFT from their wallet 120 (e.g., wallet 120-5) to a wallet 120 associated with the healthcare provider system 130 (e.g., wallet 120-3). Similarly, upon removal of the implant from the patient, the healthcare provider system 130 may transfer the NFT associated with the removed implant from wallet 120-3 to wallet 120-4. By transferring NFTs associated with defective and out of inventory medical implants, the medical implant and health tracking system 100 can track not only medical devices in circulation but also those that have been taken out of circulation because of removal from the patient or a determination that the respective medical device is defective prior to implantation.

In some embodiments, once the medical device has arrived at the healthcare provider, the medical device may be prepared for implantation into a patient (e.g., user). The patient may be prompted to register a user device (e.g., user device 140) with medical device and health tracking system 100 to generate a wallet 120-5 associated with the patient/user. The user may be able to encrypt access to the wallet 120-5 with the use of numerous known security methods. For example, the user may use a password to encrypt access to wallet 120-5 via user device 140. In other examples, the user may be required to input a seed phrase in order to access wallet 120-5. Various forms of biometric inputs can be used to encrypt access to the wallet 120-5, for example, a fingerprint scan, a retinal scan, or any other bio-unique property to the individual. When it is time to implant the medical device into a patient/user, the NFT can be prepared to be transferred from wallet 120-3 to wallet 120-5. The transfer may be preapproved by a patient using their user device 140 (e.g., user device 140-1). In some embodiments, to improve accuracy of NFT transfers to accurately reflect the medical device being implanted into the user/patient, two or more employees/agents of the healthcare provider system 130 may be required to effectuate the transfer of the NFT from the wallet 120-3 to wallet 120-5. In some embodiments, the patient may also need to approve the transfer of the NFT from wallet 120-3 to wallet 120-5 (e.g., via the use of user device 140-1).

Once a medical device is implanted and the NFT is transferred to the wallet 120-5 associated with the patient/user, the medical device and health tracking system 100 is configured to facilitate numerous patient-centric functionalities. For example, data present within the NFT can be encrypted and not accessible by entities outside of the user/patient unless prior authorization is given to these entities. For example, the user can, via user 140-1, selectively grant authorization to other entities such as other users (e.g., users associated with user devices 140-2, 140-3, ..., 140-N), and/or healthcare provider system 130, study sponsor system 160, insurance provider system 170, manufacturer system 180, and/or distributor system 190.

In some embodiments, users can receive compensation or credit for granting access to the data stored within the NFT. In some embodiments, the compensation may be provided in the form of a cryptocurrency token, a stable coin, USD, or other method of exchanging value.

The user may also select different levels of access to grant to other entities. For example, the user may grant access to only some data within the NFT and not other data entries. In some examples, the user can grant read-only access in which the entity can view data entries within the NFT but cannot edit the NFT. In other examples, the user may grant editor-level access to an NFT in which the entity being granted access can edit the data contained within the NFT. In any case, the user can also specify what data within the NFT is shared, and can limit the access in time (e.g., limiting access to a specific time period).

The NFT stored within wallet 120-5 can give the user (e.g., via user device 140-1) numerous benefits. The user may be notified by the medical device and health tracking system 100 when the warranty associated with the medical device is about to expire. The medical device and health tracking system 100 can compare the warranty term as stored in the NFT to the current date to determine that the warranty is nearing expiration and transmit a notification to the user via user device 140-1. In another example, the medical device and health tracking system 100 can transmit a notification to the patient regarding the status of the medical device. For example, the user device 140-1 can receive a notification when it is time for a pacemaker to receive a battery replacement, or when it is time to change the flow rate of a ventriculoperitoneal (VP) shunt. The medical device and health tracking system 100 can also transmit a notification to user device 140-1 when a certain procedure is due to maintain the medical device implanted within the user. For example, a certain implant may require MRI evaluation every number of years, and this requirement may be stored as a data point within the NFT stored on wallet 120-5 associated with the user/patient. The medical device and health tracking system 100 may transmit a notification to the user via user device 140-1 when it is time to perform the procedure associated with the medical device. In a similar manner, a healthcare provider associated with the healthcare provider system 130 can update the NFT with an indication that the procedure has been performed and/or that the status of the medical device has changed (e.g., battery has been changed of the pacemaker, flow rate has been changed of the VP shunt, etc.).

In certain example embodiments the user may receive notifications indicating a medical device is defective, and notification regarding the potential to share information with third parties for some form of compensation, each described in more detail below.

In certain example embodiments, the user can provide a third party access to some of the information stored within the NFT on wallet 120-5. As described above, the access can be limited in time, in scope of data shared, and can be editor-level or read only access. In some examples, third party access can be granted to another user (e.g., via user device 140-2), thereby allowing a user of user device 140-2 access to some or all of the data within the NFT. This may be useful for the purpose of a child sharing medical information with a parent or guardian, a patient sharing medical information with a conservator or with a person the patient has granted power of attorney. This feature may allow a trusted individual to have access to a patient's data stored within the NFT in the event the patient is unable to manage their own data. In some embodiments, when data is shared with a third party (e.g., user device 140-2), the medical device and health tracking system 100 can create copy of the NFT within wallet 120-5 and can transfer that copy into a new wallet 120-6 that is associated with user device 140-2. The copy can be a partial copy including only some data within the original NFT, or can be a complete copy of the NFT containing all the data within the original NFT. The copy can also be limited in time and/or revocable, while in other embodiments, the copy stored in wallet 120-6 can be permanent.

According to some embodiments, a manufacturer (e.g., via manufacturer system 180) may provide information regarding recalls that would require a medical device to be removed. The medical device and health tracking system 100 may compare the data within the recall request to the data stored within the NFTs throughout all wallets 120. When the medical device and health tracking system 100 identifies one or more NFTs that have data matching the recall request, users may be notified of the recall request via user devices 140. Users can grant access to various third parties, such as the manufacturer system 180 and/or the insurance provider system 170 so that recall information can be more accurately tracked to determine incidence rates and other possible contraindications for some patients. In certain example embodiments, wallets 120 can also store NFTs related to other non-medical device related health information, as will be further described below. If a user receives a diagnosis that is stored within an NFT, the user can share the NFT with the diagnosis with a third party to improve care outcomes, and/or to allow third parties to determine correlations between certain health conditions and a medical device implanted within a user.

In some embodiments, wallet 120 can store additional data that is not directly related to a medical device. The wallet 120 can store additional data including health related information of the user that is not related to a medical device. In this regard, wallet 120 can store an NFT containing information including diagnoses, health conditions, medication lists, etc. The wallet 120 can contain other associated medical comorbidities similar to the contents of a healthcare provider EMR. These data entries may be contained within an NFT that is stored on tracking system 110. As an example, a wallet 120 may include a diagnoses of congestive heart failure, the date of the diagnosis, and the diagnosing physician. In addition, the NFT may contain images of the heart, echocardiograms, results of bloodwork and/or other indicating lab tests supporting the diagnosis. In addition, blockchain 110 can store data associated with medications that a user/patient is prescribed. In some embodiments, the user can provisionally edit the medication list to indicate whether the user is actively taking the prescribed medication or whether the medication is inactive. In such example embodiments, medical device and health tracking system 100 may require that the edit to the medication list be authenticated by the physician of the user before the edited medication list is approved.

In some embodiments, medical information stored within an NFT of wallet 120 can be categorized in at least two different categories of data. Provisional/pending data may include medical information that has been provided by the physician and has not been acknowledged by the user. Provisional/pending data may also include medical data (e.g., a potential health condition or diagnosis) that is provided by the user, but has not been verified by the physician. Another category of information may be approved/verified data. Approved/verified data may include data that has been provided by the physician and has been acknowledged by the user. Approved/verified data may also include data provided by the user/patient that has been verified by the physician.

In some embodiments, the medical information stored within an NFT of wallet 120 can be categorized into a third data type associated with disagreements. In one example, the user/patient may provisionally add a diagnosis or medical condition to the NFT of wallet 120, but the physician may disagree with the diagnosis or medical condition. This information may be listed under a "disagreement" category of medical data. In another example, the physician may provisionally add a medical diagnosis or condition that the user/patient disagrees with, which may be stored in the same "disagreement" data category of the NFT within wallet 120.

In certain example embodiments the medical device and health tracking system 100 can integrate with EMR systems of healthcare provider system 130. In some examples, a user can utilize a medical device NFT to validate the user's identity in order to receive EMR data from healthcare provider system 130 that is associated with the user. In this regard, the medical device and health tracking system 100 can validate a user (e.g., via user device 140) based on the NFT stored on the wallet 120 controlled by the user. Once the user is validated, the medical device and health tracking system 100 can transmit a request for sharing EMR data to healthcare provider system 130. Healthcare provider system 130 may transmit the EMR data to medical device and health tracking system 100, which may be used to generate an NFT that is stored on blockchain 110 within wallet 120 of the user. Optionally, validation may be performed by the healthcare provider system 130. In this regard, the user may share an NFT associated with the medical device with the healthcare provider system 130. Healthcare provider system 130 receive a temporary or permanent, partial or full, copy of the NFT on a wallet 120 associated with the healthcare provider system 130. Based on this information, healthcare provider system 130 can validate the identity of the user and then transmit EMR data to be stored on a wallet 120 associated with the user. In other embodiments, validation of the user's identity can be performed in other ways besides the sharing of the medical device NFT. For example, the user may validate his or her identity by providing medical device and tracking system 100 a username and password combination, seed phrase, or a biometric input.

In certain example embodiments, the medical device and health tracking system 100 may be used for other authentication purposes. For example, a user of the medical device and health tracking system 100 may use complete or partial, permanent or temporary, copies of the NFTs stored within their wallet 120 to prove to a third party system that the user is a human on the internet.

In certain example embodiments, copies of NFTs stored within a user's wallet 120 may be monetized by the user. For example, a user may be able to purchase a copy of an NFT associated with a celebrity's medical implant. In one example, the medical implant NFT may be associated with the breast implant of the celebrity. The celebrity may transmit a copy of the medical device NFT to the wallet 120 of a purchasing user and in response, receive payment in the form of a cryptocurrency or a stable coin to the wallet 120 of the celebrity. Notably, the celebrity may maintain the ability to "buy back" or rescind access to the copy of the medical device NFT. For example, by transmitting the same amount of cryptocurrency or stable coin to the wallet 120 of the user, the celebrity may rescind access to the copy of the medical device NFT.

In one aspect of the medical device and tracking system 100, the creation of NFTs may be used to track any item used within a medical procedure. For example, any item used in a medical procedure may be tokenized and turned into an NFT that is stored within a wallet 120 associated with a respective healthcare provider system 130. For example, when a disposable IV is used on a patient, an NFT associated with the disposable IV can be transferred from the wallet 120 of a healthcare provider system 130 to a wallet 120 associated with the user. A similar procedure can be applied to every item used within a medical procedure, such as for saline bags, medications, towels used in surgery, etc. Before arriving at the healthcare provider system 130, a manufacturer may create an NFT in a wallet 120 associated with the manufacturer system 180, which is transferred to a wallet 120 associated with the distributor system 190, and transferred again to healthcare provider system 130 upon arriving at a healthcare provider. Once the item is used in connection with a patient, the NFT associated with that item may be transferred to a user's wallet 120. The process described above may give users/patients more control over their medical information, and can increase the responsibility of healthcare providers, manufacturers, and distributors to enhance sterility of items being used in medical interventions because every item is tracked within medical device and health tracking system 100. In addition, medical device and health tracking system 100 increases the ability to trace potential issues with medical interventions if a patient has a negative health outcome. For example, if a patient is diagnosed with an infection after a medical procedure, the information stored within medical device and health tracking system 100 may be utilized to determine what items were a potential cause of the infection.

Figure 5:
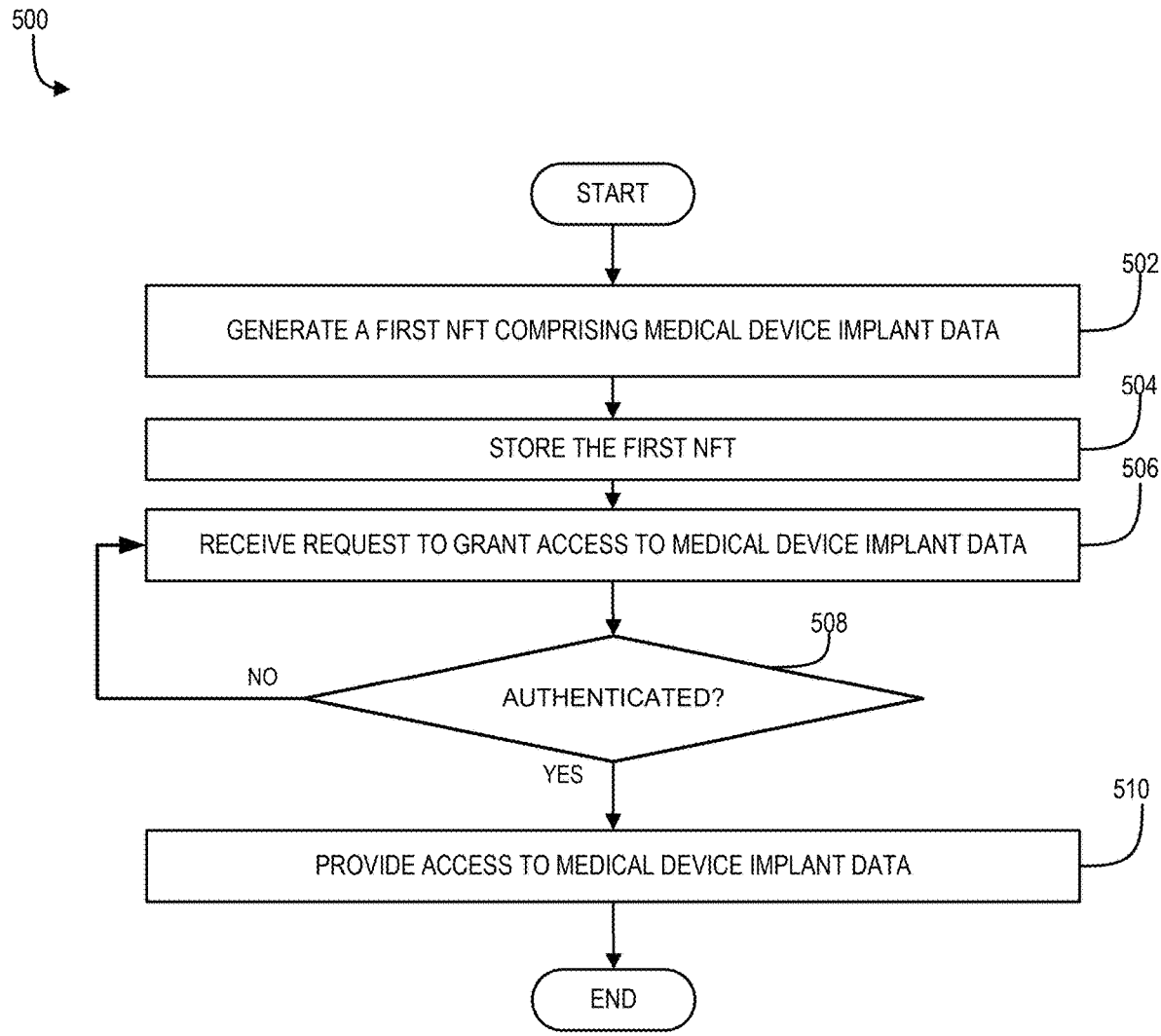
FIG. 5 is a flow diagram illustrating an exemplary method for providing access to medical device implant data stored on the medical device and health tracking system in accordance with certain embodiments of the disclosed technology.

FIG. 5 is a flow diagram illustrating an exemplary method for providing access to medical device implant data stored on the medical device and health tracking system in accordance with certain embodiments of the disclosed technology. The steps of method 500 may be performed by one or more components of the medical device and health tracking system 100 (e.g., tracking system 110, healthcare provider system 130, user devices 140, study sponsor system 160, insurance provider system 170, manufacturer system 180, and distributor system 190, as described in more detail with respect to FIGS. 1-4.

In block 502, the medical device and health tracking system 100 may generate a first NFT. The first NFT can include medical device data associated with a medical device implanted within a user. In this regard, the first NFT can be stored on a wallet 120 associated with the user. The wallet 120 can generate a first blockchain address and the NFT may be stored on the first blockchain address that may be controlled by the wallet 120.

In block 504, the medical device and health tracking system 100 may store the first NFT on a first blockchain address on tracking system 110. The first blockchain address can be generated by, and associated with the wallet 120 associated with the user. In this regard, the first NFT can be stored on a wallet 120 associated with the user. The wallet 120 can generate a first blockchain address and the NFT may be stored on the first blockchain address that may be controlled by the wallet 120.

In block 506, the medical device and health tracking system 100 can receive a request to grant access to a second user (e.g., via user device 140-2 or healthcare provider system 130) medical device implant data from a user device (e.g., user device 140-1) associated with the user.

In decision block 508, the medical device and health tracking system 100 may determine an authentication level granted to the second user. The authentication level granted to the second user may be determined based in part on the request to grant access from block 506. In response to determining that the second user is not authenticated, the method may move back to block 506. In response to determining that the second user is authenticated, the method may move to block 510.

In block 510, the medical device and health tracking system 100 may provide access to the medical device implant data within the NFT. The medical device and health tracking system 100 may grant varying levels of access to the medical device implant data. For example, the system may grant only partial access to the data stored within the NFT of wallet 120. In another example, the access may be time limited (e.g., automatically revoked after a certain amount of time). The level of access may be based on the request to grant access in block 506. In other words, the first user may specify the level of access to be granted to the second user. After block 510, method 500 may end.

Figure 10:
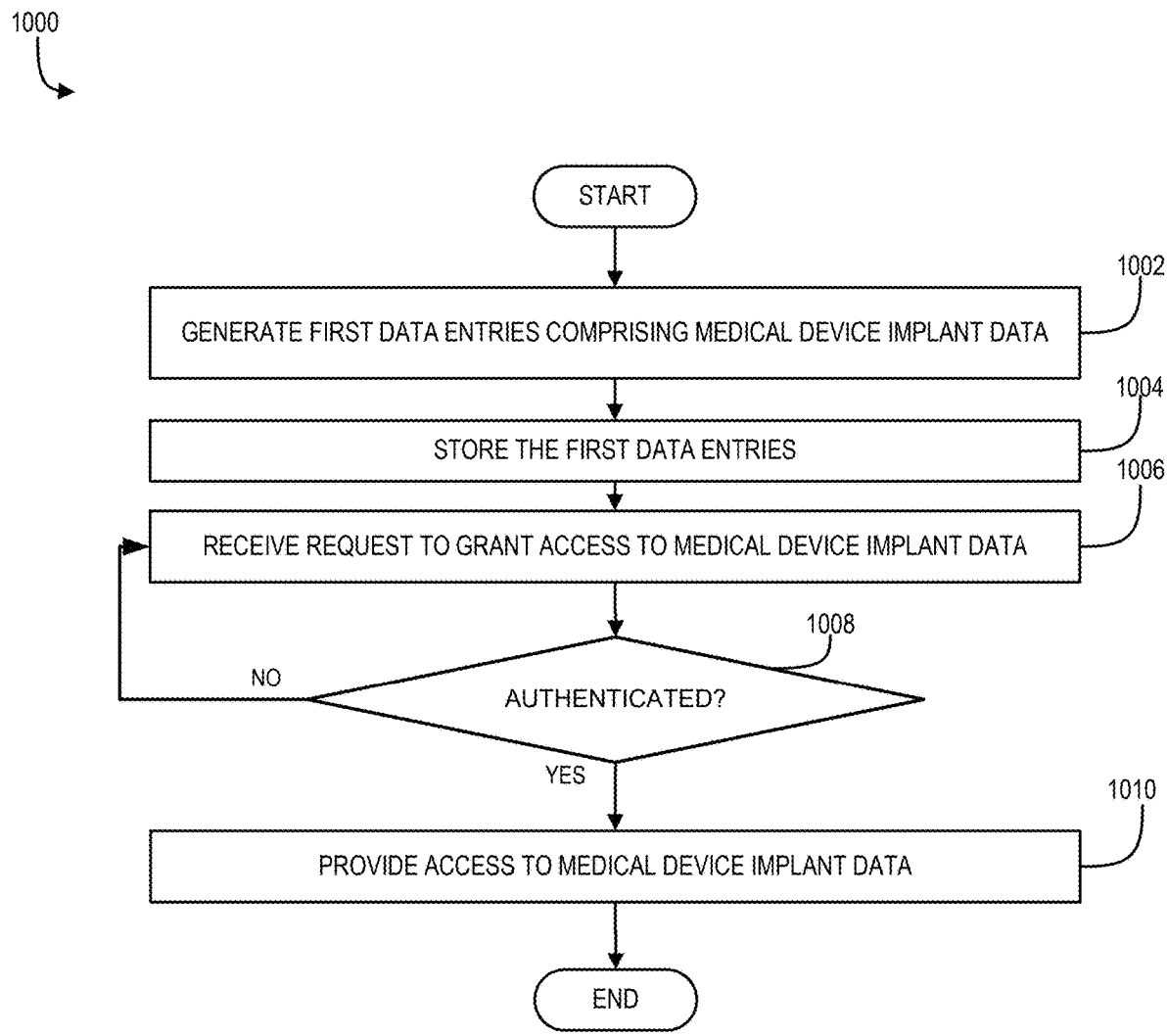
FIG. 10 is a flow diagram illustrating an exemplary method for providing access to medical device implant data stored on the medical device and health tracking system, in accordance with certain embodiments of the disclosed technology.

FIG. 10 is a flow diagram illustrating an exemplary method 1000 for providing access to medical device implant data stored on the medical device and health tracking system in accordance with certain embodiments of the disclosed technology. The steps of method 1000 may be performed by one or more components of the medical device and health tracking system 700 (e.g., tracking system 710, healthcare provider system 130, user devices 140, study sponsor system 160, insurance provider system 170, manufacturer system 180, and distributor system 190, as described in more detail with respect to FIGS. 7-9. Blocks 506 and 510 of FIG. 5 are identical to blocks 1006 and 1010 of FIG. 11, and therefore a full description is omitted here for brevity.

In block 1002, the system may generate one or more first data entries. The one or more data entries can include medical device data associated with a medical device implanted within a user. In this regard, and as shown in block 1004, the one or more first data entries can be stored on a wallet 120 associated with the user.

In decision block 1008, the medical device and health tracking system 700 may determine an authentication level granted to the second user. The authentication level granted to the second user may be determined based in part on the request to grant access from block 1006. In response to determining that the second user is not authenticated, the method may move back to block 1006. In response to determining that the second user is authenticated, the method may move to block 1010.

Figure 6:
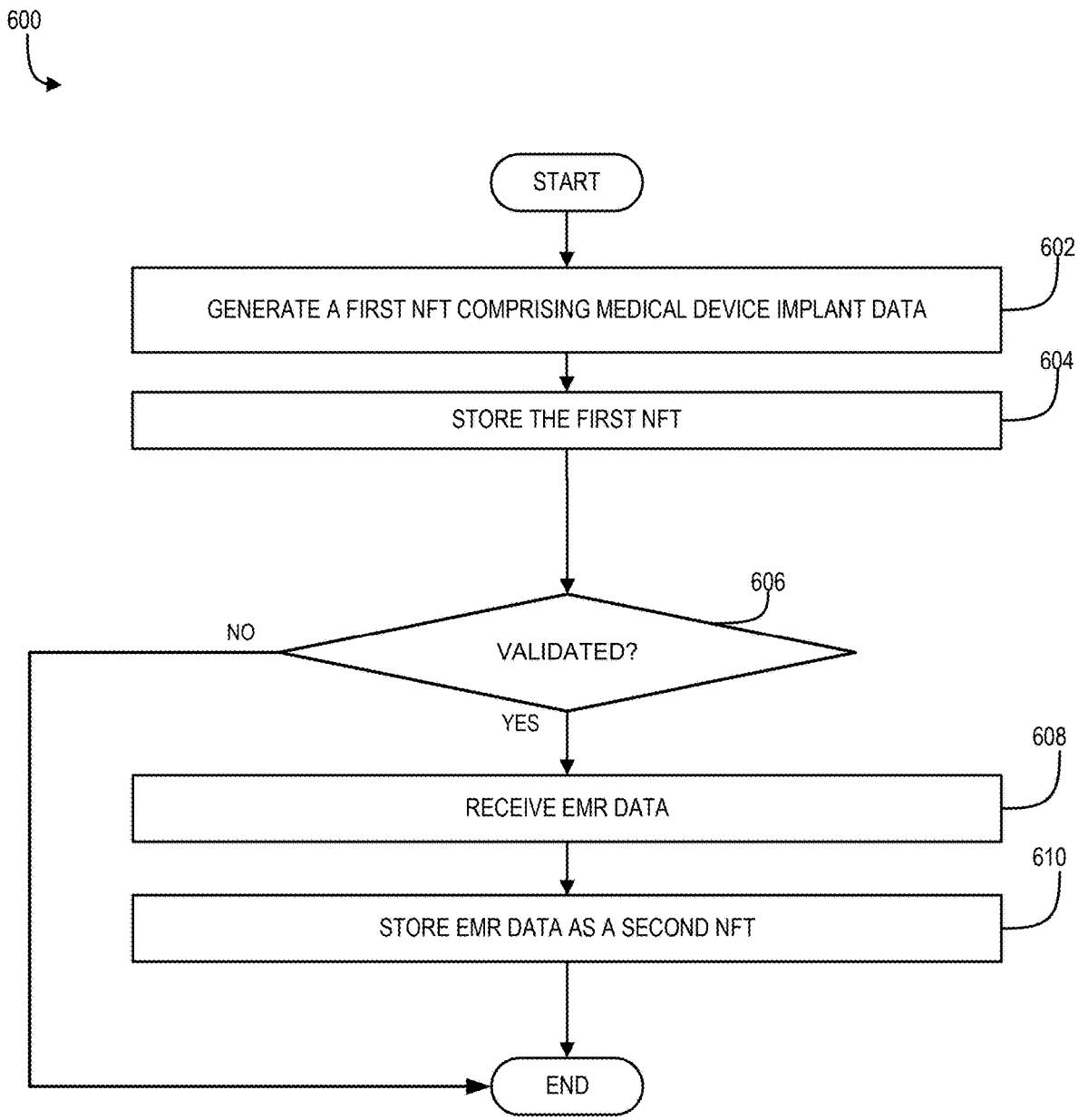
FIG. 6 is a flow diagram illustrating an exemplary method for storing and providing access to medical health data by the medical device and health tracking system in accordance with certain embodiments of the disclosed technology.

FIG. 6 is a flow diagram illustrating an exemplary method for storing and providing access to medical health data by the medical device and health tracking system in accordance with certain embodiments of the disclosed technology. The steps of method 600 may be performed by one or more components of the medical device and health tracking system 100 (e.g., tracking system 110, healthcare provider system 130, user devices 140, study sponsor system 160, insurance provider system 170, manufacturer system 180, and distributor system 190, as described in more detail with respect to FIGS. 1-4.

In block 602, the medical device and health tracking system 100 may generate a first NFT. The first NFT can include medical device data associated with a medical device implanted within a user.

In block 604, the medical device and health tracking system 100 may store the first NFT on a first blockchain address on tracking system 110. The first blockchain address can be generated by, and associated with the wallet 120 associated with the user. In this regard, the first NFT can be stored on a wallet 120 associated with the user. The wallet 120 can generate a first blockchain address and the NFT may be stored on the first blockchain address that may be controlled by the wallet 120.

In decision block 606, the medical device and health tracking system 100 may validate the identity of the user. The medical device and health tracking system 100 may validate the identity based on the first NFT generated in block 602. In some embodiments, the identity of the user may be validated based on other means, such as a username/password combination input by the user to a first user device 140-1, a biometric input, a seed phrase, etc.

In response to the medical device and health tracking system 100 not being able to validate the first user, method 600 may end. In response to medical implant and health tracking system 100 successfully validating the first user, the method may move to block 608.

In block 608, based on successfully validating the identity of the first user, the medical device and health tracking system 100 may receive EMR data. The EMR data may be received from a healthcare provider (e.g., healthcare provider system 130). In this regard, the medical device and health tracking system 100 may transmit a request for the EMR data from the healthcare provider system 130. In response, the healthcare provider system 130 may transmit the EMR data associated with the user to the medical device and health tracking system 100.

In block 610, the medical device and health tracking system 100 may store the EMR data as a second NFT on tracking system 110. The second NFT may be stored within a wallet 120 associated with the first user. In this regard, the wallet 120 may generate a blockchain address (e.g., a second blockchain address) and the tracking system 110 may store the second NFT on the second blockchain address. In some embodiments, the second NFT may be stored on the first blockchain address, but in any case, the second NFT may be stored within wallet 120 that is associated with the user. After block 610, the method 600 may end.

Figure 11:
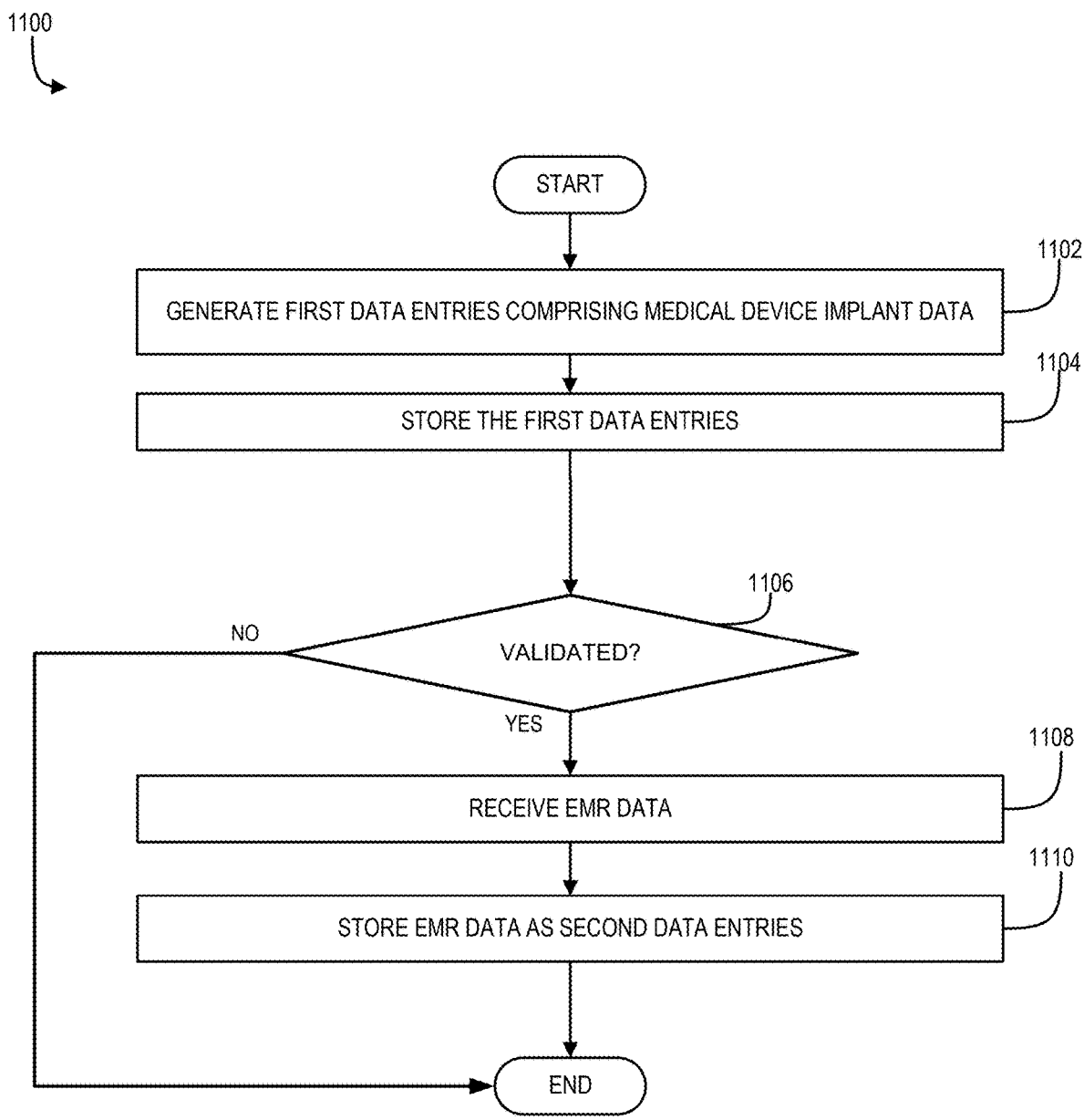
FIG. 11 is a flow diagram illustrating an exemplary method for storing and providing access to medical health data by the medical device and health tracking system, in accordance with certain embodiments of the disclosed technology.

FIG. 11 is a flow diagram illustrating an exemplary method for storing and providing access to medical health data by the medical device and health tracking system in accordance with certain embodiments of the disclosed technology. The steps of method 1100 may be performed by one or more components of the medical device and health tracking system 700 (e.g., tracking system 710, healthcare provider system 130, user devices 140, study sponsor system 160, insurance provider system 170, manufacturer system 180, and distributor system 190, as described in more detail with respect to FIGS. 7-9. Block 608 of FIG. 6 is identical to block 1108 of FIG. 11, and therefore a full description is omitted here for brevity.

In block 1102, the system may generate one or more first data entries. The one or more data entries can include medical device data associated with a medical device implanted within a user. In this regard, and as shown in block 1104, the one or more first data entries can be stored on a wallet 120 associated with the user.

In decision block 1106, the medical device and health tracking system 700 may validate the identity of the user. The medical device and health tracking system 700 may validate the identity based on the one or more first data entries generated in block 602. In some embodiments, the identity of the user may be validated based on other means, such as a username/password combination input by the user to a first user device 140-1, a biometric input, a seed phrase, etc.

In block 1110, the medical device and health tracking system 700 may store the EMR data as one or more second data entries on tracking system 710. The one or more second data entries may be stored within a wallet 120 associated with the first user. After block 1110, the method 600 may end.

Figure 12:
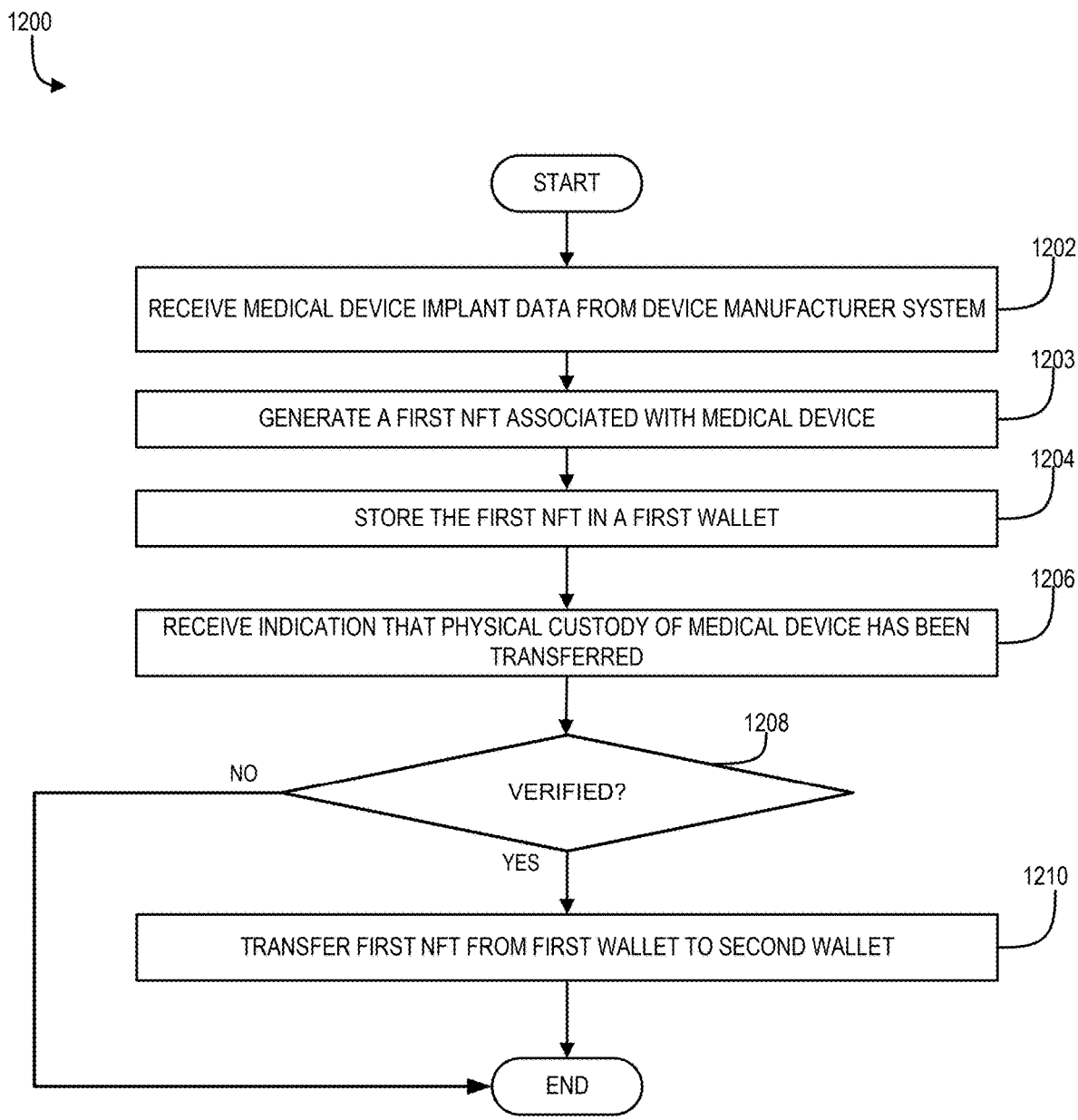
FIG. 12 is a flow diagram illustrating an exemplary method for electronically tracking a physical custody transfer of a medical device by the medical device and health tracking system, in accordance with certain embodiments of the disclosed technology.

FIG. 12 is a flow diagram illustrating an exemplary method 1200 for storing and providing access to medical health data by the medical device and health tracking system in accordance with certain embodiments of the disclosed technology. The steps of method 1200 may be performed by one or more components of the medical device and health tracking system 100 (e.g., tracking system 110, healthcare provider system 130, user devices 140, study sponsor system 160, insurance provider system 170, manufacturer system 180, and distributor system 190, as described in more detail with respect to FIGS. 1-4.

In block 1202, the medical device and health tracking system may receive medical device implant data from a device manufacturer system. In this regard, upon the manufacture of a medical device, the medical device may become associated with an identifier (e.g., a QR code) that encodes data describing characteristics of the medical device. An associate of the device manufacturer system may scan the QR code and transmit the encoded to the medical device and health tracking system.

In block 1203, the medical device and health tracking system can generate a first NFT associated with the medical device. In this regard, the first NFT contains the data received from the device manufacture system.

In block 1204, the system may store the first NFT on a first blockchain address on tracking system 110. The first blockchain address can be generated by, and associated with the wallet 120 associated with the device manufacturer system. In this regard, the first NFT can be stored on a wallet 120 associated with the device manufacturer system. The wallet 120 can generate a first blockchain address and the NFT may be stored on the first blockchain address that may be controlled by the wallet 120.

In block 1206, the system may receive an indication that physical custody of the medical device has been transferred to another entity (e.g., one of a distributor system 190, healthcare provider system 130, or a patient associated with at least one patient user device 140. The indication of a physical custody transfer may be received by the system in response to an associate of the transferee interacting with the medical device (e.g., by scanning a QR code associated with the medical device).

In block 1208, the system may verify that physical custody of the medical device has been transferred based on the information received in block 1206. If the system cannot verify that the transfer has occurred (e.g., when a threshold number of associates do not interact with the medical device identifier), method 1200 may end. In response to verifying that the physical transfer has occurred (e.g., when a threshold number of associates interact with the medical device identifier), the method may move to block 1210.

In block 1210, the system may transfer the first NFT from the first wallet to a second wallet. In this regard, the system may transfer the first NFT to a second blockchain address on tracking system 110. The second blockchain address can be generated by, and associated with the wallet 120 associated with entity receiving physical custody.

Figure 13:
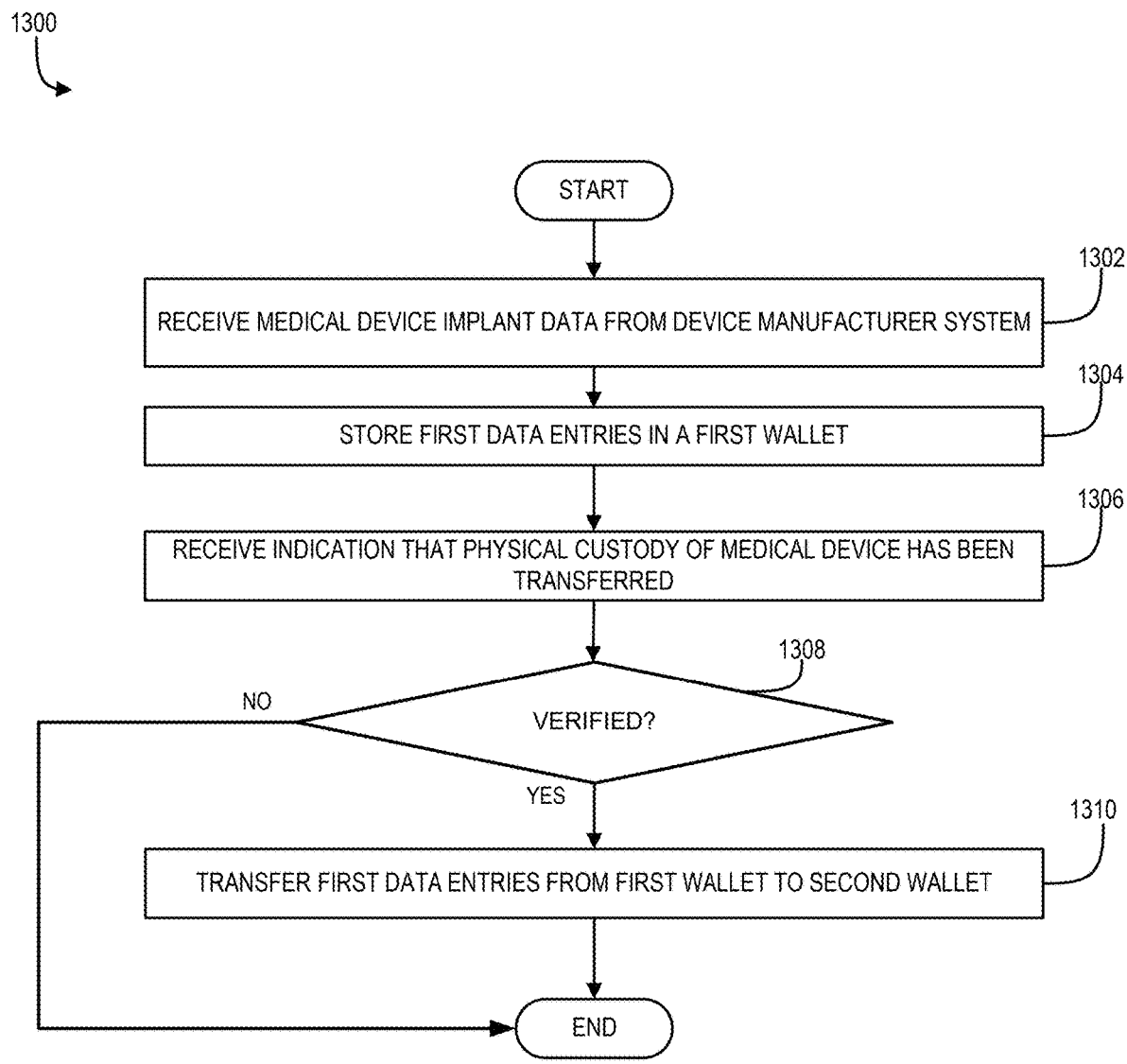
FIG. 13 is a flow diagram illustrating an exemplary method for electronically tracking a physical custody transfer of a medical device by the medical device and health tracking system, in accordance with certain embodiments of the disclosed technology.

FIG. 13 is a flow diagram illustrating an exemplary method 1300 for storing and providing access to medical health data by the medical device and health tracking system in accordance with certain embodiments of the disclosed technology. The steps of method 1300 may be performed by one or more components of the medical device and health tracking system 700 (e.g., tracking system 710, healthcare provider system 130, user devices 140, study sponsor system 160, insurance provider system 170, manufacturer system 180, and distributor system 190, as described in more detail with respect to FIGS. 7-9. Blocks 1202, 1206, and 1208 of FIG. 12 are identical to blocks 1302, 1305, and 1308 of FIG. 13, and therefore a full description is omitted here for brevity.

In block 1304, the system may store the medical device implant data as one or more first data entries on tracking system 710 within wallet 120.

In block 1310, the system may transfer the one or more first data entries from the first wallet to a second wallet. In this regard, control of the digital representation of the medical device may be transferred from the device manufacture system to the entity receiving physical custody of the medical device.

In some examples, disclosed systems or methods may involve one or more of the following clauses:

Clause 1: A medical device tracking system comprising: one or more processors; and one or more non-transitory memories in communication with the one or more processors storing instructions thereon that when executed by the one or more processors are configured to cause the system to: generate a first non-fungible token (NFT) associated with a medical device implanted within a first user, the first NFT comprising medical device implant data; store the first NFT on a first blockchain address on a blockchain; receive, from a first user device associated with the first user, a request to grant access to a first portion of the medical device implant data to a second user device associated with a second user; determine, based on an authentication level of the second user, the first portion of medical device implant data to provide to the second user device; and provide access to the first portion of medical device implant data to the second user device.

Clause 2: The medical device tracking system of clause 1, wherein the second user device is associated with a healthcare provider system.

Clause 3: The medical device tracking system of clause 2, wherein the one or more non-transitory memories include further instructions, that when executed by the one or more processors, are configured to cause the system to: receive, from the second user device, additional data associated with a health condition of the first user; receive, from the first user device, an acknowledgement of the additional data; generate a second NFT associated with the additional data; and store the second NFT on a second blockchain address on the blockchain.

Clause 4: The medical device tracking system according to any of clauses 2-3, wherein the one or more non-transitory memories include further instructions, that when executed by the one or more processors, are configured to cause the system to: receive, from the first user device, additional data associated with a potential health condition associated with the first user; receive, from the second user device, a confirmation of the additional data; generate a second NFT associated with the additional data; and store the second NFT on a second blockchain address on the blockchain.

Clause 5: The medical device tracking system of clause 4, wherein the second user device is granted a data access level selected from read only access and editor access.

Clause 6: The medical device tracking system according to any of clauses 1-5, wherein the one or more non-transitory memories include further instructions, that when executed by the one or more processors, are configured to cause the system to: receive, from a third user device associated with a third user, a study initiation request associated with a medical device type; determine based on comparing the medical device type to the stored first NFT, that the medical device implanted within the first user is associated with the medical device type; and transmit, to the first user device, an indication that the medical device implanted within the first user is compatible with the study initiation request.

Clause 7: The medical device tracking system of clause 6, wherein the one or more non-transitory memories include further instructions, that when executed by the one or more processors, are configured to cause the system to: receive, from the first user device, a request to grant access to the medical device implant data to the third user device; determine, based on an authentication level of the third user, a second portion of medical device implant data to provide to the third user; and provide access to the second portion of medical device implant data to the third user device.

Clause 8: The medical device tracking system of clause 7, wherein the one or more non-transitory memories include further instructions, that when executed by the one or more processors, are configured to cause the system to receive, at a second blockchain address associated with the first user, one or more cryptocurrency tokens in response to providing access to the second portion of medical device implant data to the third user device.

Clause 9: The medical device tracking system of clause 8, wherein the one or more cryptocurrency tokens comprise one or more stable coins.

Clause 10: The medical device tracking system according to any of clauses clause 2-9, wherein the one or more non-transitory memories include further instructions, that when executed by the one or more processors, are configured to cause the system to: authenticate a first user device based on the first NFT; receive EMR data from the second user device; and store the EMR data as a second NFT associated on a second blockchain address on the blockchain, wherein the first blockchain address and the second blockchain address are associated with the first user.

Clause 11: The medical device tracking system according to any of clauses 1-10, wherein the one or more non-transitory memories include further instructions, that when executed by the one or more processors, are configured to cause the system to: receive, from the first user device, a warranty request associated with the medical device implanted within the user; validate the warranty request based on data stored in the first NFT; and transmit the warranty request to a third user device associated with a manufacturer of the medical device implanted within the user.

Clause 12: The medical device tracking system according to any of clauses 1-11, wherein the one or more non-transitory memories include further instructions, that when executed by the one or more processors, are configured to cause the system to: receive, from a third user device associated with a manufacturer of the medical device implanted within the user, a recall request; validate the recall request based on data stored in the first NFT; and transmit a notification to the first user device regarding the recall request.

Clause 13: A medical device tracking system comprising: one or more processors; and one or more non-transitory memories in communication with the one or more processors storing instructions thereon that when executed by the one or more processors are configured to cause the system to: generate a first non-fungible token (NFT) associated with a medical device implanted within a first user, the first NFT comprising medical device implant data; store the first NFT on a first blockchain address on a blockchain; validate the first user based on first NFT, the first user associated with a first user device; receive EMR data from a second user device associated with a healthcare provider system; and store the EMR data as a second NFT associated on a second blockchain address on the blockchain, wherein the first blockchain address and the second blockchain address are associated with the first user.

Clause 14: The medical device tracking system of clause 13, wherein the one or more non-transitory memories include further instructions, that when executed by the one or more processors, are configured to cause the system to: receive, from the first user device, a request to grant access to a first portion the medical device implant data to the second user device; determine, based on an authentication level of the second user, the first portion of medical device implant data to provide to the second user; and provide access to the first portion of medical device implant data to the second user device.

Clause 15: A method comprising: generating a first non-fungible token (NFT) associated with a medical device implanted within a first user, the first NFT comprising medical device implant data; storing the first NFT on a first blockchain address on a blockchain, wherein the first blockchain address is associated with the first user; receiving, from a first user device associated with the first user, a request to grant access to a first portion of the medical device implant data to a second user device associated with a second user; determining, based on an authentication level of the second user, the first portion of medical device implant data to provide to the second user; and providing access to the first portion of medical device implant data to the second user device.

Clause 16: The method of clause 15, wherein the second user device is associated with a healthcare provider system.

Clause 17: The method of clause 16, further comprising: receiving, from the second user device, additional data associated with a health condition of the first user; receiving, from the first user device, an acknowledgement of the additional data; generating a second NFT associated with the additional data; and storing the second NFT on a second blockchain address on the blockchain, wherein the second blockchain address is associated with the first user.

Clause 18: The method according to any of clauses 16-17, further comprising: receiving, from the first user device, additional data associated with a potential health condition associated with the first user; receiving, from the second user device, a confirmation of the additional data; generating a second NFT associated with the additional data; and storing the second NFT on a second blockchain address on the blockchain, wherein the second blockchain address is associated with the first user.

Clause 19: The method according to any of clauses 15-18, further comprising: receiving, from a third user device associated with a third user, a study initiation request associated with a medical device type; determining, based on comparing the medical device type to the stored first NFT, that the medical device implanted within the first user is associated with the medical device type; and transmitting, to the first user device, an indication that the medical device implanted within the first user is compatible with the study initiation request.

Clause 20: The method of clause 19, further comprising: receiving, from the first user device, a request to grant access to the medical device implant data to the third user device; determining, based on an authentication level of the third user, a second portion of medical device implant data to provide to the third user; providing access to the second portion of medical device implant data to the third user device; and receiving, at a second blockchain address associated with the first user, one or more cryptocurrency tokens in response to providing access to the second portion of medical device implant data to the third user device.

Clause 21: A method comprising: receiving, from a device manufacturer system, medical device implant data identifying a first medical device that has been manufactured; generating a first non-fungible token (NFT) associated with the first medical device, the first NFT comprising the medical device implant data; storing the first NFT in a first wallet associated with the device manufacturer system; receiving an indication that physical custody of the first medical device has been transferred from the device manufacturer system to a second entity; receiving, from one or more first user devices, verification of a physical custody transfer from the device manufacturer system to the second entity; and responsive to the verification, transferring the first NFT from the first wallet to a second wallet associated with the second entity.

Clause 22: The method of clause 21, wherein the second entity comprises a hospital system responsible for implantation of the first medical device into a first patient.

Clause 23: The method of clause 22, further comprising: receiving an indication from one or more second user devices verifying that the first medical device has been implanted into the first patient; responsive to receiving the indication, transferring the first NFT from the second wallet to a third wallet associated with the first patient.

Clause 24: The method according to any of clauses 22-23, further comprising: receiving, from one or more third user devices, an indication that the first medical device is defective; and transferring the first NFT from the second wallet to a fourth wallet configured to track defective inventory.

Clause 25: The method according to any of clauses 23-24, wherein the first medical device comprises a first machine-readable identifier and verifying that the first medical device has been implanted into the first patient comprises receiving, from the one or more second user devices, an indication that the one or more second user devices have interacted with the first machine-readable identifier.

Clause 26: The method according to any of clauses 21-25, further comprising: receiving, from the second entity, an indication that a first user device of the one or more first user devices is no longer associated with the second entity; and removing the first user device from the one or more first user devices.

Clause 27: A medical device tracking system comprising: one or more processors; and one or more non-transitory memories in communication with the one or more processors storing instructions thereon that when executed by the one or more processors are configured to cause the system to: generate one or more first data entries associated with a medical device implanted within a first user, the one or more first data entries comprising medical device implant data; store the one or more first data entries within a first wallet associated with the first user; receive, from a first user device associated with the first user, a request to grant access to a first portion of the medical device implant data to a second user device associated with a second user; determine, based on an authentication level of the second user, the first portion of medical device implant data to provide to the second user device; and provide access to the first portion of medical device implant data to the second user device.

Clause 28: The medical device tracking system of clause 27, wherein the second user device is associated with a healthcare provider system.

Clause 29: The medical device tracking system of clause 28, wherein the one or more non-transitory memories include further instructions, that when executed by the one or more processors, are configured to cause the system to: receive, from the second user device, additional data associated with a health condition of the first user; receive, from the first user device, an acknowledgement of the additional data; generate one or more second data entries associated with the additional data; and store the one or more second data entries within the first wallet.

Clause 30: The medical device tracking system of clause 28 or clause 29, wherein the one or more non-transitory memories include further instructions, that when executed by the one or more processors, are configured to cause the system to: receive, from the first user device, additional data associated with a potential health condition associated with the first user; receive, from the second user device, a confirmation of the additional data; generate one or more second data entries associated with the additional data; and store the one or more second data entries within the first wallet.

Clause 31: The medical device tracking system of clause 30, wherein the second user device is granted a data access level selected from read only access and editor access.

Clause 32: The medical device tracking system according to any of clauses 27-31, wherein the one or more non-transitory memories include further instructions, that when executed by the one or more processors, are configured to cause the system to: receive, from a third user device associated with a third user, a study initiation request associated with a medical device type; determine based on comparing the medical device type to the one or more first data entries, that the medical device implanted within the first user is associated with the medical device type; and transmit, to the first user device, an indication that the medical device implanted within the first user is compatible with the study initiation request.

Clause 33: The medical device tracking system of clause 32, wherein the one or more non-transitory memories include further instructions, that when executed by the one or more processors, are configured to cause the system to: receive, from the first user device, a request to grant access to the medical device implant data to the third user device; determine, based on an authentication level of the third user, a second portion of medical device implant data to provide to the third user; and provide access to the second portion of medical device implant data to the third user device.

Clause 34: The medical device tracking system of clause 33, wherein the one or more non-transitory memories include further instructions, that when executed by the one or more processors, are configured to cause the system to receive, by the first wallet, one or more tokens in response to providing access to the second portion of medical device implant data to the third user device.

Clause 35: The medical device tracking system of clause 34, wherein the one or more tokens are selected from fiat currency, stable coins, and cryptocurrency tokens.

Clause 36: The medical device tracking system according to any of clauses 28-35, wherein the one or more non-transitory memories include further instructions, that when executed by the one or more processors, are configured to cause the system to: authenticate a first user device based on the one or more first data entries; receive EMR data from the second user device; and store the EMR data as one or more second data entries within the first wallet.

Clause 37: The medical device tracking system according to any of clauses 27-36, wherein the one or more non-transitory memories include further instructions, that when executed by the one or more processors, are configured to cause the system to: receive, from the first user device, a warranty request associated with the medical device implanted within the user; validate the warranty request based on data stored in the one or more first data entries; and transmit the warranty request to a third user device associated with a manufacturer of the medical device implanted within the user.

Clause 38: The medical device tracking system according to any of clauses 27-37, wherein the one or more non-transitory memories include further instructions, that when executed by the one or more processors, are configured to cause the system to: receive, from a third user device associated with a manufacturer of the medical device implanted within the user, a recall request; validate the recall request based on data stored in the one or more first data entries; and transmit a notification to the first user device regarding the recall request.

Clause 39: A medical device tracking system comprising: one or more processors; and one or more non-transitory memories in communication with the one or more processors storing instructions thereon that when executed by the one or more processors are configured to cause the system to: generate one or more first data entries associated with a medical device implanted within a first user, the one or more first data entries comprising medical device implant data; store the one or more first data entries within a first wallet associated with the first user; validate a first user device based on the one or more first data entries, the first user device associated with the first user; receive EMR data from a second user device associated with a healthcare provider system; and store the EMR data as one or more second data entries within the first wallet associated with the first user.

Clause 40: The medical device tracking system of clause 39, wherein the one or more non-transitory memories include further instructions, that when executed by the one or more processors, are configured to cause the system to: receive, from the first user device, a request to grant access to a first portion of the medical device implant data to the second user device; determine, based on an authentication level of the second user, the first portion of medical device implant data to provide to the second user device; and provide access to the first portion of medical device implant data to the second user device.

Clause 41: A method comprising: generating one or more first data entries associated with a medical device implanted within a first user, the one or more first data entries comprising medical device implant data; storing the one or more first data entries within a first wallet associated with the first user; receiving, from a first user device associated with the first user, a request to grant access to a first portion of the medical device implant data to a second user device associated with a second user; determining, based on an authentication level of the second user, the first portion of medical device implant data to provide to the second user; and providing access to the first portion of medical device implant data to the second user device.

Clause 42: The method of clause 41, wherein the second user device is associated with a healthcare provider system.

Clause 43: The method of clause 42, further comprising: receiving, from the second user device, additional data associated with a health condition of the first user; receiving, from the first user device, an acknowledgement of the additional data; generating one or more second data entries associated with the additional data; and storing the one or more second data entries within the first wallet.

Clause 44: The method according to any of clauses 42-43, further comprising: receiving, from the first user device, additional data associated with a potential health condition associated with the first user; receiving, from the second user device, a confirmation of the additional data; generating one or more second data entries associated with the additional data; and storing the one or more second data entries within the first wallet.

Clause 45: The method according to any of clauses 41-44, further comprising: receiving, from a third user device associated with a third user, a study initiation request associated with a medical device type; determining, based on comparing the medical device type to the one or more first data entries, that the medical device implanted within the first user is associated with the medical device type; and transmitting, to the first user device, an indication that the medical device implanted within the first user is compatible with the study initiation request.

Clause 46: The method of clause 45, further comprising: receiving, from the first user device, a request to grant access to the medical device implant data to the third user device; determining, based on an authentication level of the third user, a second portion of medical device implant data to provide to the third user; providing access to the second portion of medical device implant data to the third user device; and receiving, by the first wallet, one or more tokens in response to providing access to the second portion of medical device implant data to the third user device.

Clause 47: A method comprising: receiving, from a device manufacturer system, medical device implant data identifying a first medical device that has been manufactured; storing the medical device implant data as one or more first data entries in a first wallet associated with the device manufacturer system; receiving an indication that physical custody of the first medical device has been transferred from the device manufacturer system to a second entity; receiving, from one or more first user devices, verification of a physical custody transfer from the device manufacturer system to the second entity; and responsive to the verification, transferring the one or more data entries from the first wallet to a second wallet associated with the second entity.

Clause 48: The method of clause 47, wherein the second entity comprises a hospital system responsible for implantation of the first medical device into a first patient.

Clause 49: The method of clause 48, further comprising: receiving an indication from one or more second user devices verifying that the first medical device has been implanted into the first patient; responsive to receiving the indication, transferring the one or more first data entries from the second wallet to a third wallet associated with the first patient.

Clause 50: The method according to any of clauses 48-49, further comprising: receiving, from one or more third user devices, an indication that the first medical device is defective; and transferring the one or more first data entries from the second wallet to a fourth wallet configured to track defective inventory.

Clause 51: The method of clause 49, wherein the first medical device comprises a first machine-readable identifier and verifying that the first medical device has been implanted into the first patient comprises receiving, from the one or more second user devices, an indication that the one or more second user devices have interacted with the first machine-readable identifier.

Clause 52: The method according to any of clauses 47-51, further comprising: receiving, from the second entity, an indication that a first user device of the one or more first user devices is no longer associated with the second entity; and removing the first user device from the one or more first user devices.

The features and other aspects and principles of the disclosed embodiments may be implemented in various environments. Such environments and related applications may be specifically constructed for performing the various processes and operations of the disclosed embodiments or they may include a general-purpose computer or computing platform selectively activated or reconfigured by program code to provide the necessary functionality. Further, the processes disclosed herein may be implemented by a suitable combination of hardware, software, and/or firmware. For example, the disclosed embodiments may implement general purpose machines configured to execute software programs that perform processes consistent with the disclosed embodiments. Alternatively, the disclosed embodiments may implement a specialized apparatus or system configured to execute software programs that perform processes consistent with the disclosed embodiments. Furthermore, although some disclosed embodiments may be implemented by general purpose machines as computer processing instructions, all or a portion of the functionality of the disclosed embodiments may be implemented instead in dedicated electronics hardware.

The disclosed embodiments also relate to tangible and non-transitory computer readable media that include program instructions or program code that, when executed by one or more processors, perform one or more computer-implemented operations. The program instructions or program code may include specially designed and constructed instructions or code, and/or instructions and code well-known and available to those having ordinary skill in the computer software arts. For example, the disclosed embodiments may execute high level and/or low-level software instructions, such as machine code (e.g., such as that produced by a compiler) and/or high-level code that can be executed by a processor using an interpreter.

As used in this application, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Certain embodiments and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

As an example, embodiments or implementations of the disclosed technology may provide for a computer program product, including a computer-usable medium having a computer-readable program code or program instructions embodied therein, said computer-readable program code adapted to be executed to implement one or more functions specified in the flow diagram block or blocks. Likewise, the computer program instructions may be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

Certain implementations of the disclosed technology described above with reference to user devices may include mobile computing devices. Those skilled in the art recognize that there are several categories of mobile devices, generally known as portable computing devices that can run on batteries but are not usually classified as laptops. For example, mobile devices can include, but are not limited to portable computers, tablet PCs, internet tablets, PDAs, ultra-mobile PCs (UMPCs), wearable devices, and smart phones.

In this description, numerous specific details have been set forth. It is to be understood, however, that implementations of the disclosed technology may be practiced without these specific details. In other instances, well-known methods, structures, and techniques have not been shown in detail in order not to obscure an understanding of this description. References to "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form. By "comprising" or "containing" or "including" is meant that at least the named element, or method step is present in article or method, but does not exclude the presence of other elements or method steps, even if the other such elements or method steps have the same function as what is named.

It is to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Although embodiments are described herein with respect to systems or methods, it is contemplated that embodiments with identical or substantially similar features may alternatively be implemented as systems, methods and/or non-transitory computer-readable media.

As used herein, unless otherwise specified, the use of the ordinal adjectives "first," "second," "third," etc., to describe a common object, merely indicates that different instances of like objects are being referred to, and is not intended to imply that the objects so described must be in a given sequence, either temporally, spatially, in ranking, or in any other manner.

While certain embodiments of this disclosure have been described in connection with what is presently considered to be the most practical and various embodiments, it is to be understood that this disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the technology and also to enable any person skilled in the art to practice certain embodiments of this technology, including making and using any apparatuses or systems and performing any incorporated methods. The patentable scope of certain embodiments of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A medical device tracking system comprising:
   one or more processors; and
   one or more non-transitory memories in communication with the one or more processors storing instructions thereon that when executed by the one or more processors are configured to cause the system to:
   generate a first non-fungible token (NFT) associated with a medical device implanted within a first user, the first NFT comprising medical device implant data;
   store the first NFT on a first blockchain address on a blockchain;

receive, from a first user device associated with the first user, a request to grant access to a first portion of the medical device implant data to a second user device associated with a second user;

determine, based on an authentication level of the second user, the first portion of medical device implant data to provide to the second user device;

provide access to the first portion of medical device implant data to the second user device;

receive, from a third user device associated with a third user, a study initiation request associated with a medical device type;

determine based on comparing the medical device type to the stored first NFT, that the medical device implanted within the first user is associated with the medical device type; and transmit, to the first user device, an indication that the medical device implanted within the first user is compatible with the study initiation request.

2. The medical device tracking system of claim 1, wherein the second user device is associated with a healthcare provider system.

3. The medical device tracking system of claim 2, wherein the one or more non-transitory memories include further instructions, that when executed by the one or more processors, are configured to cause the system to:

receive, from the second user device, additional data associated with a health condition of the first user;

receive, from the first user device, an acknowledgement of the additional data;

generate a second NFT associated with the additional data; and store the second NFT on a second blockchain address on the blockchain.

4. The medical device tracking system of claim 2, wherein the one or more non-transitory memories include further instructions, that when executed by the one or more processors, are configured to cause the system to:

receive, from the first user device, additional data associated with a potential health condition associated with the first user;

receive, from the second user device, a confirmation of the additional data;

generate a second NFT associated with the additional data; and store the second NFT on a second blockchain address on the blockchain.

5. The medical device tracking system of claim 4, wherein the second user device is granted a data access level selected from read only access and editor access.

6. The medical device tracking system of claim 1, wherein the one or more non-transitory memories include further instructions, that when executed by the one or more processors, are configured to cause the system to:

receive, from the first user device, a request to grant access to the medical device implant data to the third user device;

determine, based on an authentication level of the third user, a second portion of medical device implant data to provide to the third user; and provide access to the second portion of medical device implant data to the third user device.

7. The medical device tracking system of claim 6, wherein the one or more non-transitory memories include further instructions, that when executed by the one or more processors, are configured to cause the system to receive, at a second blockchain address associated with the first user, one or more cryptocurrency tokens in response to providing access to the second portion of medical device implant data to the third user device.

8. The medical device tracking system of claim 7, wherein the one or more cryptocurrency tokens comprise one or more stable coins.

9. The medical device tracking system of claim 2, wherein the one or more non-transitory memories include further instructions, that when executed by the one or more processors, are configured to cause the system to:

authenticate a first user device based on the first NFT;

receive EMR data from the second user device; and store the EMR data as a second NFT associated on a second blockchain address on the blockchain, wherein the first blockchain address and the second blockchain address are associated with the first user.

10. The medical device tracking system of claim 1, wherein the one or more non-transitory memories include further instructions, that when executed by the one or more processors, are configured to cause the system to:

receive, from the first user device, a warranty request associated with the medical device implanted within the user;

validate the warranty request based on data stored in the first NFT; and transmit the warranty request to a third user device associated with a manufacturer of the medical device implanted within the user.

11. The medical device tracking system of claim 1, wherein the one or more non-transitory memories include further instructions, that when executed by the one or more processors, are configured to cause the system to:

receive, from a third user device associated with a manufacturer of the medical device implanted within the user, a recall request;

validate the recall request based on data stored in the first NFT; and transmit a notification to the first user device regarding the recall request.

12. A method comprising:

generating a first non-fungible token (NFT) associated with a medical device implanted within a first user, the first NFT comprising medical device implant data;

storing the first NFT on a first blockchain address on a blockchain, wherein the first blockchain address is associated with the first user;

receiving, from a first user device associated with the first user, a request to grant access to a first portion of the medical device implant data to a second user device associated with a second user;

determining, based on an authentication level of the second user, the first portion of medical device implant data to provide to the second user;

providing access to the first portion of medical device implant data to the second user device;

receiving, from a third user device associated with a third user, a study initiation request associated with a medical device type;

determining, based on comparing the medical device type to the stored first NFT, that the medical device implanted within the first user is associated with the medical device type; and transmitting, to the first user device, an indication that the medical device implanted within the first user is compatible with the study initiation request.

13. The method of claim 12, wherein the second user device is associated with a healthcare provider system.

14. The method of claim 13, further comprising:
receiving, from the second user device, additional data associated with a health condition of the first user;
receiving, from the first user device, an acknowledgement of the additional data;
generating a second NFT associated with the additional data; and
storing the second NFT on a second blockchain address on the blockchain, wherein the second blockchain address is associated with the first user.

15. The method of claim 13, further comprising:
receiving, from the first user device, additional data associated with a potential health condition associated with the first user;
receiving, from the second user device, a confirmation of the additional data;
generating a second NFT associated with the additional data; and
storing the second NFT on a second blockchain address on the blockchain, wherein the second blockchain address is associated with the first user.

16. The method of claim 12, further comprising:
receiving, from the first user device, a request to grant access to the medical device implant data to the third user device;
determining, based on an authentication level of the third user, a second portion of medical device implant data to provide to the third user;
providing access to the second portion of medical device implant data to the third user device; and
receiving, at a second blockchain address associated with the first user, one or more cryptocurrency tokens in response to providing access to the second portion of medical device implant data to the third user device.

\* \* \* \* \*